(12) United States Patent
Kondo et al.

(10) Patent No.: US 12,031,136 B2
(45) Date of Patent: Jul. 9, 2024

(54) TREATMENT FOR SKELETAL DISEASES CAUSED BY INTRACELLULAR PROTEIN TRAFFICKING DEFECTS

(71) Applicants: Oklahoma Medical Research Foundation, Oklahoma City, OK (US); The Board of Regents of the University of Oklahoma, Norman, OK (US)

(72) Inventors: Yuji Kondo, Oklahoma City, OK (US); Jianxin Fu, Oklahoma City, OK (US); Hua Wang, Oklahoma City, OK (US); Klaas Wierenga, Oklahoma City, OK (US); Patrick M. Gaffney, Oklahoma City, OK (US); Lijun Xia, Oklahoma City, OK (US)

(73) Assignees: Oklahoma Medical Research Foundation, Oklahoma City, OK (US); The Board of Regents of the University of Oklahoma, Norman, OK (US)

( * ) Notice: Subject to any disclaimer, the term of this patent is extended or adjusted under 35 U.S.C. 154(b) by 511 days.

(21) Appl. No.: 16/758,339

(22) PCT Filed: Oct. 23, 2018

(86) PCT No.: PCT/US2018/057131
§ 371 (c)(1),
(2) Date: Apr. 22, 2020

(87) PCT Pub. No.: WO2019/084024
PCT Pub. Date: May 2, 2019

(65) Prior Publication Data
US 2020/0339997 A1 Oct. 29, 2020

Related U.S. Application Data

(60) Provisional application No. 62/576,360, filed on Oct. 24, 2017.

(51) Int. Cl.
*A61K 31/192* (2006.01)
*A61K 31/155* (2006.01)
(Continued)

(52) U.S. Cl.
CPC ........ *C12N 15/1137* (2013.01); *A61K 31/155* (2013.01); *A61K 31/18* (2013.01);
(Continued)

(58) Field of Classification Search
CPC ......... A61P 19/08; A61P 19/00; A61K 31/192
See application file for complete search history.

(56) References Cited

U.S. PATENT DOCUMENTS

| 8,883,148 B2 * | 11/2014 | Chung ................ A61K 9/0019 514/561 |
| 9,339,520 B2 | 5/2016 | Edinger et al. |
| 2013/0116300 A1 | 5/2013 | Collard et al. |

FOREIGN PATENT DOCUMENTS

| WO | 2016112350 A1 | 7/2016 | |
| WO | WO-2016112350 A1 * | 7/2016 | ......... A61K 31/7088 |
| WO | 2019084024 A1 | 5/2019 | |

OTHER PUBLICATIONS

Gioia et al. Human Molecular Genetics, 2017, vol. 26, No. 15, pp. 2897-2911. (Year: 2017).*
(Continued)

*Primary Examiner* — Craig D Ricci
*Assistant Examiner* — Janet L Coppins
(74) *Attorney, Agent, or Firm* — Edwin S. Flores; Daniel J. Chalker; Chalker Flores, LLP

(57) ABSTRACT

The present invention includes a method of treating a bone disease caused by a intracellular protein trafficking defect comprising: identifying a subject having the bone disease caused by the intracellular protein trafficking defect in a membrane bound transcription factor peptidase, site 1 (MB-
(Continued)

TPS1) gene; and providing the subject with an effective amount of a composition that bypasses or corrects a defect in MBTPS1 gene expression, gene splicing, or corrects protein trafficking defects in the endoplasmic reticulum and to the lysosome.

3 Claims, 26 Drawing Sheets

Specification includes a Sequence Listing.

(51) Int. Cl.
| | |
|---|---|
| A61K 31/18 | (2006.01) |
| A61K 31/26 | (2006.01) |
| A61K 31/4045 | (2006.01) |
| A61K 31/436 | (2006.01) |
| A61K 31/575 | (2006.01) |
| A61K 38/05 | (2006.01) |
| A61K 38/07 | (2006.01) |
| A61K 38/08 | (2019.01) |
| A61P 19/08 | (2006.01) |
| C12N 15/113 | (2010.01) |
| C12N 15/64 | (2006.01) |
| A61K 45/06 | (2006.01) |

(52) U.S. Cl.
CPC ............ *A61K 31/192* (2013.01); *A61K 31/26* (2013.01); *A61K 31/4045* (2013.01); *A61K 31/436* (2013.01); *A61K 31/575* (2013.01); *A61K 38/05* (2013.01); *A61K 38/07* (2013.01); *A61K 38/08* (2013.01); *A61P 19/08* (2018.01); *C12N 15/64* (2013.01); *A61K 45/06* (2013.01)

(56) References Cited

OTHER PUBLICATIONS

Brown, M., et al., "The SREBP Pathway: Regulation of Cholesterol Metabolism by Proteolysis of a Membrane-Bound Transcription Factor" Cell, vol. 89, May 2, 1997, pp. 331-340.
International Search Report and Written Opinion of PCT/US2018/057131 of USPTO dated May 3, 2019 (13 pp.).
Ishikawa, T., et al. "UPR transducer BBF2H7 allows export of type II collagen in a cargo- and developmental stage-specific manner," J. Cell Biol., vol. 216, No. 6, 2017, pp. 1761-1774.
Ishikawa, T., et al. "Intracellular mechanisms of molecular recognition and sorting for transport of large extracellular matrix molecules," PNAS, Sep. 27, 2016, pp. E6036-E6044.
Kole, R., et al., "RNA therapeutics: Beyond RNA interference and antisense oligonucleotides," Nat. Ref. Drug Discov. vol. 11(2), pp. 125-140, Feb. 5, 2016.
Kudo, M., et al., "Mucolipidosis II (I-Cell disease) and Mucolipidosis IIIA (Classical Pseudo-Hurler Polydystrophy) Are Caused by Mutations in the GlcNAc-Phosphotransferase a/B-Subunits Precursor Gene," Am. J. Hum. Genet., Jan. 24, 2006, vol. 78, pp. 451-463.
Marschner, K., et al. "A Key Enzyme in the Biogenesis of Lysosomes Is a Protease That Regulates Cholesterol Metabolism," Science, vol. 333, Jul. 1, 2011 pp. 87-90.
Oida, Y., et al. "Post-treatment of a BiP inducer prevents cell death after middle cerebral artery occlusion in mice," Neuroscience Letters, vol. 484, Aug. 6, 2010, pp. 43-46.
Patra, D., et al., "Site-1 protease is essential for endochondral bone formation in mice," J. Cell Biol., vol. 179, No. 4, Nov. 19, 2007, pp. 687-700.
Tiede, S., et al., "Mucolipidosis II is caused by mutations in GNPTA encoding the α/β GlcNAc-1-phosphotransferase," Nature Medicine Letters, Volume 11, No. 10, Oct. 2005, pp. 1109-1112.
Yang, J., et al., "Decreased lipid synthesis in livers of mice with disrupted Site-1 protease gene," PNAS, vol. 98, No. 24, Nov. 20, 2001, pp. 13607-13612.
Ye, J., et al., ER Stress Induces Cleavage of Membrane-Bound ATF6 by the Same Proteases that Process SREBPs, Molecular Cell, vol. 6, Dec. 2000, pp. 1355-1364.
Baljet, B., Aspects of the history of Osteogenesis imperfecta (Vrolik's syndrome), Annals of Anatomy, (22) 184, pp. 1-7.
Biggin, A., et al., "Osteogenesis Imperfecta: Diagnosis Treatment," Curr Osteoporos Rep, Jun. 26, 2014, vol. 12, pp. 279-288.
Bishop, N., "Characterising and treating osteogenesis imperfecta," Early Human Development, vol. 86, (2010), pp. 743-746.
Evans, CH., et al., "Osteoarthritis gene therapy," Gene Therapy, 2004, vol. 11, pp. 379-389.
Hoyer-Kuhn, H., et al., "Osteogenesis imperfecta: pathophysiology and treatment," Wien Med Wochenschr (2015), vol. 165, pp. 278-284.
Michael, Joern W.-P.,"The Epidemiology, Etiology, Diagnosis, and Treatment of Osteoarthritis of the Knee," Continuing Medical Education, Dtsch Arztebl Int 2010, 107(9), pp. 152-162.
Sovani, S., et al., "Osteoarthritis Detection, Pathophysiology, and Current/Future Treatment Strategies," Orthopaedic Nursing, Jan./Feb. 2013, vol. 32:1, pp. 25-36.
Achilleos, A., et al., "MBTPS1/SKI-1/S1P proprotein convertase is required for ECM signaling and axial elongation during somitogenesis and vertebral development," Human Molecular Genetics, vol. 24, No. 10, Feb. 2015, pp. 2884-2898.
Bohnert, K., et al., "Inhibition of ER Stress and unfolding protein response pathways causes skeletal muscle wasting during cancer cachexia," The FASEB Journal, Jan. 22, 2019, pp. 3053-3068.
Supplementary European Search Report for 18869891.4 dated Nov. 3, 2021, 28 pp.
Kondo, Y., et al., Site-1 protease deficiency causes human skeletal dysplasia due to defective inter-organelle protein trafficking, JCI Insight, vol. 3(14), Jul. 25, 2018, 18 pp.
Kondo, Y., Abstracts, Glycobiology: Program and Abstracts for 2018 Annual Meeting of the Socity for Glycobiology, SFG 2018, pp. 1009-1010.
Paton, L., et al., "A Novel Mouse Model of a Patient Mucolipidosis II Mutation Recapitulates Disease Pathology," The Journal of Biological Chemistry, vol. 289, No. 39, Sep. 26, 2014, pp. 26709-26721.
Abstract Only—Patra, D., Osteoarthritis and Cartilage, vol. 25, 2017, pp. S51-S52.
Rellmann, Y., et al., "Review: ER stress-induced cell death in osteoarthritic cartilage," Cellular Signalling, vol. 78, Dec. 2020, 10 pp.

\* cited by examiner

SEQUENCE LISTING

<160> NUMBER OF SEQ ID NOS: 27

<210> SEQ ID NO 1
<211> LENGTH: 24
<212> TYPE: PRT
<213> ORGANISM: Artificial Sequence
<220> FEATURE:
<223> OTHER INFORMATION: Synthetic peptide

<400> SEQUENCE: 1

Arg Arg Arg Gln Arg Arg Lys Lys Arg Gly Tyr Gly Gly Asp His Trp
1               5                   10                  15

Ile His Phe Thr Ala Asn Trp Val

```
                20

<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
cctgctggat tacatcaaag cactg                                       25

<210> SEQ ID NO 3
<211> LENGTH: 25
<212> TYPE: DNA
<213> ORGANISM: Artificial Sequence
<220> FEATURE:
<223> OTHER INFORMATION: Synthetic primer

<400> SEQUENCE: 3
gtcaagggca tatcctacaa caaac                                       25

<210> SEQ ID NO 4
<211> LENGTH: 20
<212> TYPE: DNA
<213> ORGANISM: Artificial Sequence
<220> FEATURE:
<223> OTHER INFORMATION: Synthetic primer

<400> SEQUENCE: 4
tccaattgct tggatgacag                                             20

<210> SEQ ID NO 5
<211> LENGTH: 20
<212> TYPE: DNA
<213> ORGANISM: Artificial Sequence
<220> FEATURE:
<223> OTHER INFORMATION: Synthetic primer

<400> SEQUENCE: 5
tccagaacct tggagtaccg                                             20

<210> SEQ ID NO 6
<211> LENGTH: 20
<212> TYPE: DNA
<213> ORGANISM: Artificial Sequence
<220> FEATURE:
<223> OTHER INFORMATION: Synthetic primer

<400> SEQUENCE: 6
acgctgcagg gtctgtactt                                             20

<210> SEQ ID NO 7
<211> LENGTH: 20
<212> TYPE: DNA
<213> ORGANISM: Artificial Sequence
<220> FEATURE:
<223> OTHER INFORMATION: Synthetic primer

<400> SEQUENCE: 7
acaggtcctt ctggtggttg                                             20

<210> SEQ ID NO 8
<211> LENGTH: 20
<212> TYPE: DNA
<213> ORGANISM: Artificial Sequence
```

```
<220> FEATURE:
<223> OTHER INFORMATION: Synthetic primer

<400> SEQUENCE: 8
accaaagaca tgcatggaca                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic primer

<400> SEQUENCE: 9
cacaaactgg attgcaccac                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
agccagcaga tcgagaacat                                                    20

<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
tcttgtcctt ggggttcttg                                                    20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
tagcgtatgg tgctgctgtc                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
tttgtcaggg gtctttcacc                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
cagaaccagc agaggtcaca                                                    20
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
tcaccattcg gtcaatcaga                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
gacgaggcaa gagtttcacc                                              20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer

<400> SEQUENCE: 17
gcctggggtc tgtaatctga                                              20

<210> SEQ ID NO 18
<211> LENGTH: 19
<212> TYPE: DNA
<213> ORGANISM: Artificial Sequence
<220> FEATURE:
<223> OTHER INFORMATION: Synthetic primer

<400> SEQUENCE: 18
cagttgggag taatgcaag                                               19

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
gcctggataa cctctgtg                                                18

<210> SEQ ID NO 20
<211> LENGTH: 20
<212> TYPE: DNA
<213> ORGANISM: Artificial Sequence
<220> FEATURE:
<223> OTHER INFORMATION: Synthetic primer

<400> SEQUENCE: 20
aggaatgcct gtgtctgctt                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic primer
```

<400> SEQUENCE: 21
acaggcctac ccaaacatga                                              20

<210> SEQ ID NO 22
<211> LENGTH: 21
<212> TYPE: DNA
<213> ORGANISM: Artificial Sequence
<220> FEATURE:
<223> OTHER INFORMATION: Synthetic primer

<400> SEQUENCE: 22
ggaaggcaga atccaaagac g                                            21

<210> SEQ ID NO 23
<211> LENGTH: 20
<212> TYPE: DNA
<213> ORGANISM: Artificial Sequence
<220> FEATURE:
<223> OTHER INFORMATION: Synthetic primer

<400> SEQUENCE: 23
atgccgacac aaaccactcg                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic primer

<400> SEQUENCE: 24
ccttgaggca gaaagtggag                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic primer

<400> SEQUENCE: 25
catgggtagc gatctggttt                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic primer

<400> SEQUENCE: 26
agcagcaagc agcactacaa                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic primer

<400> SEQUENCE: 27
aggaccgagt caccatgaag                                              20

TREATMENT FOR SKELETAL DISEASES CAUSED BY INTRACELLULAR PROTEIN TRAFFICKING DEFECTS

CROSS-REFERENCE TO RELATED APPLICATIONS

This application is a National Stage of International Application of PCT/US2018/57131, filed Oct. 23, 2018, which claims the benefit of U.S. Provisional Application No. 62/576,360 filed Oct. 24, 2017. The contents of each of which are incorporated by reference in their entirety.

STATEMENT OF FEDERALLY FUNDED RESEARCH

This invention was made with government support under GM114731-01A1, and P3 OGM110766 awarded by National Institutes of Health. The government has certain rights in the invention.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Oct. 22, 2018, is named OMRF2009WO_SL.txt and is 5.51, kilobytes in size.

TECHNICAL FIELD OF THE INVENTION

The present invention relates in general to the field of skeletal dysplasia caused by defects in intracellular protein trafficking.

BACKGROUND OF THE INVENTION

Without limiting the scope of the invention, its background is described in connection with skeletal diseases.

One example, U.S. Pat. No. 9,339,520, issued to Edinger, et al., and entitled "Methods and compositions for treatment of bone defects with placental cell populations", is said to teach methods for using adherent placental stem cells and placental stem cell populations, and methods of culturing, proliferating and expanding the same, and methods of differentiating the placental stem cells. These inventors are also said to teach methods of using the placental stem cells to formulate implantable or injectable compositions suitable for administration to a subject, and methods for treating bone defects with stem cells and compositions comprising stem cells.

An example is found in International Published Application WO/2016112350, filed by Xia, et al., entitled "Methods and compositions for diagnosing and treating lysosomal storage disorders". This prior work by the present inventors is directed to a compound heterozygotic mutation in membrane-bound transcription factor peptidase site 1 (MBTPS1, one is a missense mutation, D365G, the other is a nonsense mutation). MBTPS1 encodes a membrane-bound enzyme called site-1 protease (SIP), which is a member of serine proteases that act as a proprotein convertase responsible for the cleavage of several precursor substrates such as sterol regulatory element-binding proteins (proSREBPs), proSIP, and proGNPTAB. Based on this discovery, the present disclosure provides novel therapeutic and diagnostic compositions and methods for identifying the mutations and treating subjects harboring these mutations, such as enzyme replacement therapy, the use of synthetic oligonucleotides to block cryptic splicing that results from the mutations or to otherwise modulate splicing to avoid the cryptic splicing site and compounds that modulate responses in endoplasmic reticulum (ER) stress.

However, a need remains for novel therapies and methods for effectively treating other, unrelated mutations of MBTPS1.

SUMMARY OF THE INVENTION

In one embodiment, the present invention includes a method of treating a bone disease caused by an intracellular protein trafficking defect comprising: identifying a subject having the bone disease caused by the intracellular protein trafficking defect in a membrane bound transcription factor peptidase, site 1 (MBTPS1) gene; and providing the subject with an effective amount of a composition that bypasses or corrects a defect in MBTPS1 gene expression, gene splicing, or corrects lysosomal protein trafficking. In one aspect, the composition comprises an expression vector that expresses a MBTPS1 gene. In another aspect, the composition comprises an expression vector that expresses a BBF2 human homolog on chromosome 7 (BBF2H7) transcription factor, e.g., a BBF2 human homolog on chromosome 7 (BBF2H7) transcription factor that is a constitutively active form of BBF2H7 (p60). In another aspect, the composition comprises an expression vector that expresses at least one of Sec23a, Tango1, Sedlin, or Hsp47. In another aspect, the composition comprises an endoplasmic reticulum ER chaperone corrects a defect in a mutant MBTPS1 protein. In another aspect, the composition induces immunoglobulin heavy-chain binding protein (BiP) expression. In another aspect, the composition that induces BiP expression is 1-(3,4-dihydroxy-phenyl)-2-thiocyanate-ethanone. In another aspect, the composition that induces BiP expression improves osteogenicity from mesenchymal stem cells (MSCs) differentiated from iPSCs obtained from the subject. In another aspect, the composition comprises a chemical chaperone. In another aspect, the chemical chaperone is phenylbutyrate (4-PBA), tauroursodeoxycholate (TUDCA), or valproic acid. In another aspect, the chemical chaperone is a hydroxamic acid, a belinostat (PXD101), LAQ824, a panobinostat (LBH589), or a benzamide. In another aspect, the chemical chaperone is a hydroxamate, a cyclic tetrapeptide, a depsipeptide, or an electrophilic ketone. In another aspect, the composition comprises a histone deacetylase (HDAC) inhibitor. In another aspect, the composition comprises an antisense morpholino oligonucleotide that corrects the MBTPS1 gene. In another aspect, the composition comprises an autophagy inducer. In another aspect, the composition comprises an autophagy inducer selected from Tat-D11, Rapamycin, or Metformin. In another aspect, the bone disease is a skeletal dysplasia with elevated levels of blood lysosomal enzymes. In another aspect, the bone disease is caused by increased degradation of bone matrix and apoptosis of chondrocytes. In another aspect, the bone disease is selected from at least one of osteoarthritis, chondrodysplasia, osteogenesis imperfecta, or ichthyosis follicularis with alopecia and photophobia (IFAP) syndrome. In another aspect, the bone disease is selected from at least one of Type II collagenopathy, type X collagenopathy, cartilage oligomeric matrix protein (COMP) chondrodysplasia, matrillin-3 mutations, Type I collagenopathy, SERPINH1 mutations, or CREB3L1 mutations.

In another embodiment, the present invention includes a method of detecting and treating a subject with a bone disease comprising: obtaining a biological sample from the subject; detecting if the subject has elevated levels of blood lysosomal enzymes; and treating the subject with an effective amount of a composition that bypasses or corrects a defect in an MBTPS1 gene expression, gene splicing, or prevents secretion of lysosomal enzymes. In one aspect, the method further comprises the step of detecting a defect in protein trafficking. In another aspect, the method further comprises the step of detecting a mutation in an MBTPS1 gene. In another aspect, the method further comprises the step of detecting a mutation in MBTPS1 gene splicing. In another aspect, the composition comprises an expression vector that expresses a MBTPS1 gene. In another aspect, the composition comprises an expression vector that expresses a BBF2 human homolog on chromosome 7 (BBF2H7) transcription factor. In another aspect, the BBF2 human homolog on chromosome 7 (BBF2H7) transcription factor is a constitutively active form of BBF2H7 (p60). In another aspect, the composition comprises an expression vector that expresses at least one of Sec23a, Tango1, Sedlin, or Hsp47. In another aspect, the composition comprises an endoplasmic reticulum ER chaperone corrects a defect in a mutant MBTPS1 protein. In another aspect, the composition induces immunoglobulin heavy-chain binding protein (BiP) expression. In another aspect, the composition that induces BiP expression is 1-(3,4-dihydroxy-phenyl)-2-thiocyanate-ethanone. In another aspect, the composition that induces BiP expression improves osteogenicity from mesenchymal stem cells (MSCs) differentiated from iPSCs obtained from the subject. In another aspect, the composition comprises a histone deacetylase (HDAC) inhibitor. In another aspect, the composition comprises a chemical chaperone. In another aspect, the chemical chaperone is sodium phenylbutyrate (4-PBA), tauroursodeoxycholate (TUDCA), or valproic acid. In another aspect, the chemical chaperone is a hydroxamic acid, a belinostat (PXD101), LAQ824, a panobinostat (LBH589), or a benzamide. In another aspect, the chemical chaperone is a hydroxamate, a cyclic tetrapeptide, a depsipeptide, or an electrophilic ketone. In another aspect, the composition comprises an antisense morpholino oligonucleotide that corrects the MBTPS1 gene. In another aspect, the composition comprises an autophagy inducer. In another aspect, the composition comprises an autophagy inducer is selected from Tat-D11, Rapamycin, or Metformin. In another aspect, the bone disease is a skeletal dysplasia with elevated levels of blood lysosomal enzymes. In another aspect, the bone disease is caused by increased degradation of bone matrix and apoptosis of chondrocytes. In another aspect, the bone disease is selected from at least one of osteoarthritis, chondrodysplasia, osteogenesis imperfecta, or ichthyosis follicularis with alopecia and photophobia (IFAP) syndrome. In another aspect, the bone disease is selected from at least one of Type II collagenopathy, type X collagenopathy, cartilage oligomeric matrix protein (COMP) chondrodysplasia, matrillin-3 mutations, Type I collagenopathy, SERPINH1 mutations, or CREB3L1 mutations.

In another embodiment, the present invention includes a method of evaluating a candidate drug believed to be useful in treating a bone disease, the method comprising: (a) measuring a tissue suspected of having a bone disease from a set of patients; (b) administering a candidate drug to a first subset of the patients, and a placebo to a second subset of the patients; (c) repeating step a) after the administration of the candidate drug or the placebo; and (d) determining if the candidate drug reduces at least one of bone matrix degradation or apoptosis of chondrocytes that is statistically significant as compared to any reduction occurring in the second subset of patients, wherein a statistically significant reduction indicates that the candidate drug is useful in treating the bone disease.

In another embodiment, the present invention includes a composition for the treatment of a bone disease comprising: a recombinant vector that comprises a promoter that drives the expression of a MBTPS1 gene, or a composition that bypasses or corrects a defect in MBTPS1 gene expression, gene splicing, or corrects lysosomal protein trafficking, in an amount sufficient to correct the bone disease.

BRIEF DESCRIPTION OF THE DRAWINGS

For a more complete understanding of the features and advantages of the present invention, reference is now made to the detailed description of the invention along with the accompanying figures and in which:

(FIG. 1A) The patient exhibits skeletal dysplasia with kyphoscoliosis (I) and skeletal dysplasia with dysmorphic facial features, with large ears and pectus carinatum (II). (FIG. 1B) Serum lysosomal enzyme activities. (FIG. 1C) DNA sequences of MBTPS1 exon 3 and exon 9. Letters and numbers in red indicate mutated residues and sites in the S1P protein sequence. (FIG. 1D) Pedigree of the family. The black circle indicates the patient; half-black square or circles indicate heterozygotes. (FIG. 1E) Relative MBTPS1 expression in patient B cells by qRT-PCR normalized with control B cells. A forward primer designed in exon 19 and a reverse primer designed in exon 21 of MBTPS1 were used. Mean±SEM; n=3, *P<0.01, Student's t test. Patient cells exhibited 20% MBTPS1 expression compared with irrelevant control cells. (FIG. 1F) MBTPS1 cDNA sequence. The dashed box indicates an aberrant transcript. (FIG. 1G) Diagram showing that the maternal variant creates an alternative splice donor site, resulting in the 41-bp deletion in exon 9. The asterisk indicates the premature termination created by alternative splicing causing the 41-bp deletion in exon 9.

(FIG. 2A) Representative immunofluorescence images of fibroblasts from the patient and her parents. ML-II and ML-IIIa cells are positive controls derived from patients with these conditions. Cathepsin B, lysosome enzyme; LAMP1, lysosome marker; TO-PRO, nuclear counterstaining Scale bar: 10 μm. The number of N indicates the exact number of samples. (FIG. 2B) M6P-dependent lysosomal enzyme β-hexosaminidase activity from Saos2 lysates or supernatants, as indicated. Data represent mean±SEM; n=3. *P<0.05, 1-way ANOVA followed by Student's t test. (FIG. 2C) Inter-organelle trafficking of cathepsin D. Without M6P modification cathepsin D precursor is directly secreted into extracellular space. Ionomycin triggers the release of lysosomal contents through inducing the lysosomal exocytosis of matured cathepsin D. (FIG. 2D) Western blotting of precursor (p), intermediate (i), and mature (m) forms of cathepsin D from Saos2 lysates or supernatants, with or without ionomycin treatment. The precursor form of cathepsin D was detected in supernatant from GPT-KO and S1P-KO cells. However, upon ionomycin treatment, the mature form of cathepsin D was detected in supernatant from S1P-KO cells, indicating correct targeting of cathepsin D in lysosome in S1P-KO cells. (FIG. 2E) Sera from the patient (pat) and her mother (mom) were analyzed by Western blotting (top). Lysates from Saos2 cells were used as a control. The same membrane was stained with Ponceau S to confirm equivalent loading of serum proteins (bottom). (FIG. 2F) Immunofluorescence images of WT and mutant Saos2 cells. Insets show high-magnification images of lysosomes. Scale bars: 5 μm; 125 nm (insets). Enlarged lysosomes were found in GPT-KO and S1P-KO cells. Unlike GPT-KO cells in which cathepsin D is absent in lysosomes, cathepsin D was detected in lysosomes in S1P-KO cells. (FIG. 2G) Phase-contrast images of WT and mutant Saos2 cells. Arrowheads indicate inclusion bodies. Scale bar: 10 μm.

(FIG. 3A) Supernatants from WT and mutant Saos2 cells were immunoprecipitated with anti-cathepsin D antibody (anti-CtsD) or normal goat IgG or precipitated with trichloroacetic acid (TCA)/acetone (input). M6P moieties were detected with anti-M6P. WT Saos2 cells were treated with NH4Cl to mimic ML-II/III cells (positive control). p, cathepsin D precursor. Asterisks indicate nonspecific bands. As expected, M6P moiety was detected on secreted cathepsin D from WT cells induced by NH4Cl treatment but not on secreted cathepsin D from untreated GPT-KO and S1P-KO cells. (FIG. 3B) Western blotting of M6P modification of lysates. Anti-GAPDH was used as loading control. Unlike GPT-KO cells, M6P bands were detected in lysates from S1P-KO cells. (FIG. 3C) Established clones were transfected with myc3-tagged GPT reporter (top). Cleavage of the reporter substrate in S1P-KO cells was considerably impaired but a small amount of cleaved reporter substrate was detected, supporting an alternative S1P-independent GPT-activating mechanism (bottom). (FIG. 3D) GPT activity in membrane fractions of WT cells, mutant HEK293T cells, or WT or S1P-KO Saos2 cells. Compared with WT cells, GPT-KO cells showed a substantial reduction in GPT activity, which was rescued by WT cells but not by the cleavage resistant GPT-R925A construct, which has missense mutation in the cleavage site by S1P to endow the resistance to the cleavage. Residual GPT activity was observed in S1P-KO cells, suggesting an alternative S1P-independent GPT-activating mechanism. (FIG. 3E) β-Hexosaminidase activity in lysates and culture supernatants from WT and mutant Saos2 cells. S2P-KO Saos2 cells do not show excessive secretion of β-hexosaminidase. Mean±SEM for 4 independent experiments are shown. *P<0.05, 1-way ANOVA followed by Student's t test. (FIG. 3F) Serum lysosomal enzyme activities. Nor, normal individual; Fa, father; Mo, mother; Pa, patient. S2P patient does not have lysosomal abnormality Mean±SEM for 3 independent experiments are shown. *P<0.05, 1-way ANOVA followed by Student's t test. (FIG. 3G) Models of lysosomal enzyme trafficking in WT and mutant cells.

(FIG. 4A) Hand radiographs. Arrows mark shortening in tubular bones and delayed ossification of epiphyses and carpal bones in the patient compared with a healthy girl. (FIG. 4B) Flow cytometric profiles of iPSCs derived from fibroblasts of the patient and her parents using antibodies against the pluripotent stem cell markers TRA-1-60 and SSEA4. Normal fibroblasts were used as negative controls. (FIG. 4C) Scheme of generating iPSC-derived teratomas in immune-deficient NRG mice. (FIG. 4D) Images of H&E-stained teratomas. Scale bar: 100 μm. (FIG. 4E) Representative images of teratoma tissue sections. Scale bar: 5 μm. Identical chondrocytes in the patient teratoma have enlarged calnexin+ER and enlarged Lamp1+lysosomes compared with maternal chondrocytes. Arrowheads indicate enlarged ER. (FIG. 4F) Immunofluorescence images of cartilage in teratomas. TO-PRO, nuclear staining; yellow, merged. Arrowheads indicate collagen II retained in calnexin+ ER in patient-derived cartilage. Scale bar: 10 μm. (FIG. 4G) Images of TUNEL staining of maternal and patient-derived teratomas. Scale bar: 100 μm. TUNEL+ apoptotic cells were detected in cartilages but not in noncartilaginous tissues in the patient teratoma. (FIG. 4H) Expression of COP-II vesicle-related genes in maternal and patient-derived teratoma, as measured by qRT-PCR. Each dot represents a teratoma-bearing mouse. (FIG. 4I) Confocal images of cartilage in teratomas. Scale bar: 20 μm; 6.67 μm (insets). Tango1 and Hsp47 were decreased in patient cartilages compared with maternal cartilages. All data are presented as mean±SEM of at least 3 independent experiments. *P<0.05; **P<0.01, Student's t test.

(FIG. 5A) Quantification of mean fluorescent intensity (MFI) of immunofluorescence images of collagen I in fibroblasts treated with or without TGF-β1 treatment for 48 hours. Regardless of TGF-β1 treatment, the patient fibroblasts showed accumulation of collagen-I. (FIG. 5B) Transmission electron microscopy (TEM) images of maternal and patient fibroblasts. Arrowheads indicate rough ER. Enlarged rough ER was found in patient fibroblasts compared with maternal fibroblasts. Scale bar: 500 nm. (FIG. 5C) Expression of COP-II mega vesicle-related genes in maternal and patient-derived fibroblasts, as measured by qRT-PCR, normalized to maternal fibroblasts. (FIG. 5D) Expression of collagen I (COL1A1), ER stress-related genes (HSPA5 and DDIT3), and COP-II component (SEC23A) genes in maternal and patient fibroblasts, by qRT-PCR normalized to maternal fibroblasts treated with or without TGF-β1. Compared with maternal cells, patient cells showed defective induction of UPR triggered by TGF-β1 treatment. (FIG. 5E) Western blotting of Sec23a, Tango1, and Hsp47 in fibroblasts. Mo., maternal fibroblasts; PF, PF-429242 (S1P inhibitor). (FIG. 5F) Secreted procollagen I from maternal and patient fibroblasts, treated as indicated, was measured by ELISA. PF, PF-429242. S1P-dependent collagen-I secretion is shown. (FIG. 5G) Schematic protein domain structures of BBF2H7 and the constitutively active BBF2H7 p60 mutant. S1P cleaves the luminal domain of BBF2H7 followed by cleavage of the transmembrane domain by S2P in the Golgi apparatus, resulting in translocation of the cytoplasmic domain of BBF2H7 (BBF2H7 p60) to the nucleus to promote gene expression. (FIG. 5H) Expression of COL1A1, HSPA5, DDIT3, OASIS (CREB3L1), SEC23A, and COP-II enlarging proteins (Sedlin, Tango1, and Hsp47) in BBF2H7 p60-expressing patient fibroblasts compared with uninfected cells as analyzed by quantitative RT-PCR. All data are from 3 independent experiments. *P<0.05; **P<0.01, Student's t test.

(FIG. 6A) Structure of MBTPS1 pre-mRNA in abnormal and corrected maternal transcripts. The antisense morpholino oligo (AMO) was designed to block the maternal alternative MBTPS1 splicing site. The red box indicates AMO designed to block cryptic splice site. The asterisk indicates the premature termination. AMO hampers pathogenic alternative splicing and promote correct mRNA splicing. (FIG. 6B) Maternal (blue) and patient (red) fibroblasts were treated with AMO for 12, 24, and 48 hours, and MBTPS1 expression was analyzed by qRT-PCR normalized to HPRT expression. Numbers indicate fold change compared with time 0. For total MBTPS1, a forward primer designed in exon 19 and a reverse primer designed in exon 21 of MBTPS1 were used. For MBTPS1 with Δ41 bp, a forward primer designed in the boundary of exon 7-8 and a reverse primer designed in the boundary of exon 9-10 of MBTPS1 were used. (FIG. 6C) Western blotting of endogenous BBF2H7 in AMO or control oligo-treated patient fibroblasts. PF, S1P inhibitor PF-429242. Defective S1P-dependent cleavage of BBF2H7 and improved cleavage by AMO treatment in patient fibroblasts (FIG. 6D) Secreted procollagen I from maternal and patient fibroblasts treated as indicated, was measured by ELISA. AMO treatment increased collagen I secretion in patient fi (FIG. 6E) Immunofluorescence images of collagen I in fibroblasts treated with or without the PF-429242 or the PBA for 48 hours. TO-PRO, nuclear staining Scale bar: 5 μm. Quantification of mean fluorescent intensity (MFI) of intracellular collagen I staining A dramatic decrease in collagen I in PBA-treated patient fibroblasts was seen. (FIG. 6F) A model showing how S1B deficiency causes compound defects in the ER and lysosome, leading to skeletal dysplasia. All data are from at least 3 independent experiments. Mean±SEM. *P<0.05; **P<0.01, Student's t test.

(FIG. 7A) Summary of the DNA sequences of three forms of cloned exon 9 of MBTPS1 cDNA expressed in patient fibroblasts treated with AMO. Compared with control oligo treatment, AMO treatment increased 2-fold in correctly spliced transcript. Given that 10-fold increase of total MBTPS1 expression (data not shown), the absolute maternal transcript with a missense mutation (p.D365G) is increased 20-fold compared with control oligotreated cells. (FIG. 7B) The mRNA expression of an SREBP-regulated gene (DHCR7), collagen I (COL1A1), ER stress-related genes (HSPA5 and DDIT3), the secretory component (SEC23A) and mega vesicle components (Sedlin, Tango1 and Hsp47) were analysed by quantitative RTPCR after treatment with AMO. Blue, mother; red, the patient. The number indicates the fold change relative to time 0. Data represent means±SEM; n=3. *P<0.05, **P<0.01.

DETAILED DESCRIPTION OF THE INVENTION

Figure 1A:
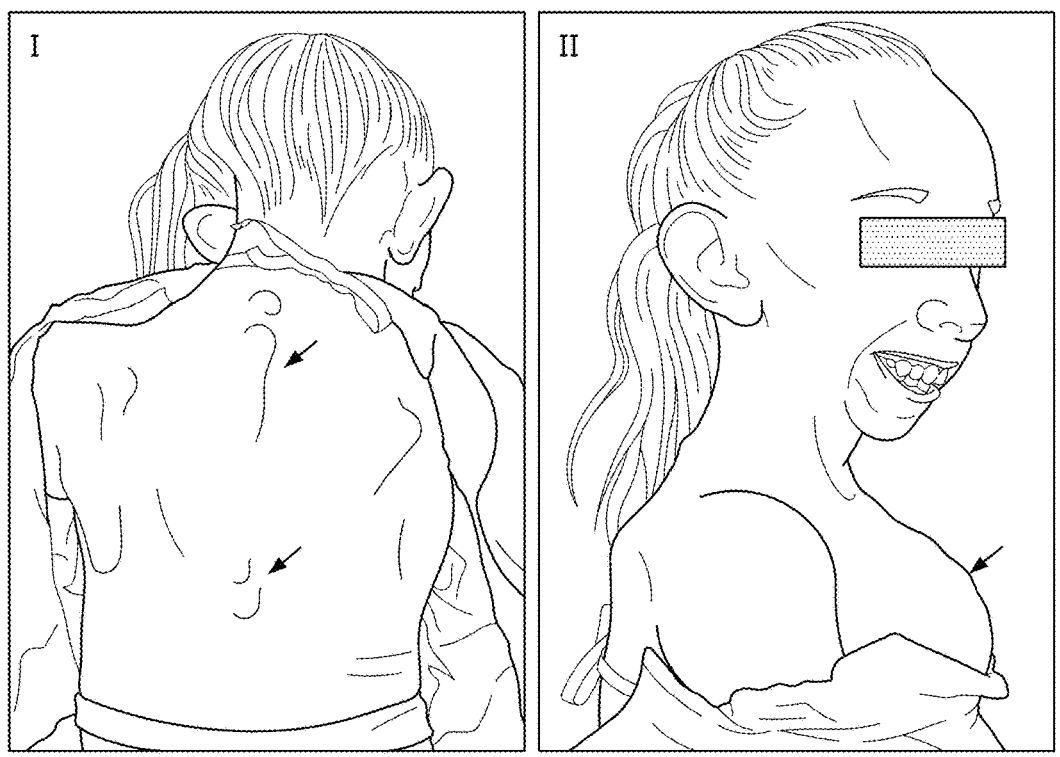
FIGS. 1A to 1G shows the identification of MBTPS1 compound heterozygote variants in a patient with skeletal dysplasia and elevated circulating levels of lysosomal enzymes.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

MBTPS1 encodes a key serine protease named site-1 protease (S1P) in the Golgi[1,2]. S1P proteolytically activates membrane-bound transcription factors such as SREBPs and ATF6 critical for cholesterol homeostasis and endoplasmic reticulum (ER) stress responses, respectively[1,3]. S1P also converts GlcNAc-1-phosphotransferase α, β (GPT) to its active form[4], which catalyzes the mannose-6-phosphate (M6P) modification of lysosomal enzymes for their targeting to the lysosome[5]. Whether defective S1P function causes human disease is unknown. Here, the inventors report an 8-year-old girl with skeletal dysplasia and elevated levels of blood lysosomal enzymes. The patient was clinically diagnosed as mucolipidosis-III (ML-III), a type of congenital lysosomal storage diseases caused by mutations of GPT encoding gene GNPTAB or GNPTG[5,6]. Unexpectedly, sequencing of these genes revealed no mutations; instead, novel compound loss-of-function heterozygous mutations in the MBTPS1 were discovered in this patient. The S1P defect causes impaired activation of GPT, resulting in increased secretion of lysosomal enzymes, and decreased S1P dependent activation of BBF2H7, a key ER stress transducer[7], leading to ER accumulation of collagens in chondrocytes. Collectively, these abnormalities lead to increased degradation of bone matrix and apoptosis of chondrocytes, causing skeletal dysplasia in the patient. Blocking aberrant splicing of MBTPS1 by antisense therapy, or reducing ER stress using small molecules, mitigates collagen trafficking defects in patient cells. Thus, these findings define a new human disorder caused by S1P deficiency, and reveal new therapeutic targets for skeletal diseases caused by similar intracellular protein trafficking defects.

As used herein, the term "endoplasmic reticulum (ER) chaperone" refers to a protein that acts as a chaperone to correct a defect caused by a mutant membrane bound transcription factor peptidase, site 1 (MBTPS1) protein, specifically, it corrects the impairment in activation of GlcNAc-1-phosphotransferase α, β (GPT) to its active form decreases secretion of lysosomal enzymes, and increases S1P mediated activation of BBF2H7, a key ER stress transducer, and prevents ER accumulation of collagens in chondrocytes. A non-limiting example of an ER chaperone is a BiP inducer X protein (BIX).

As used herein, the term "a chemical chaperone" refers to a small molecule that acts as a protein chaperone or that bypasses the decreased function of an MBTPS1 protein, specifically, it corrects the impairment in activation of GlcNAc-1-phosphotransferase α, β (GPT) to its active form decreases secretion of lysosomal enzymes, and increases S1P mediated activation of BBF2H7, a key ER stress transducer, and prevents ER accumulation of collagens in chondrocytes. Non-limiting examples of small chemical chaperones include, e.g., a histone deacetylase (HDAC) inhibitor. Examples of a histone deacetylase (HDAC) inhibitor include, e.g., phenylbutyrate (PBA), tauroursodeoxycholate (TUDCA), a valproic acid, a hydroxamic acid, a belinostat (PXD101), LAQ824, a panobinostat (LBH589), a benzamide, a hydroxamate, a cyclic tetrapeptide, a depsipeptide, or an electrophilic ketone.

As used herein, the terms "autophagy inducer" or "autophagy activator" refer to compositions that stimulate the orderly degradation and recycling of cellular components via autophagosomes. One example of an autophagy inducer is Tat-D11 (Tat-Beclin 1 D11), which is a peptide comprising 11 amino acids derived from Beclin 1 linked to the HIV Tat protein with a diglycine linker. These peptides are in a D-amino acid retro-inverso configuration and has an amino acid sequence of is RRRQRRKKRGYGGDHWIHF-TANWV (SEQ ID NO:1). Other non-limiting examples of autophagy inducers include: Rapamycin and Metformin.

As used herein, the terms "chaperone inducer" or "chaperone activator" refer to compositions that induce expression of, e.g., the endoplasmic reticulum (ER)-mediated chaperone BiP (immunoglobulin heavy-chain binding protein)/GRP78 (78 kDa glucose-regulated protein), such as BiP inducer X (BIX).

The present invention includes the discovery of novel treatments and compositions for treating diseases with abnormal ER stress and/or impaired Unfolding Protein Response (UPR). Disease related to related to abnormal ER stress include: Chondrodysplasia: Genetic and rare diseases (Type II and type X collagenopathy, COMP, matrillin-3 mutations); Osteogenesis Imperfecta (OI): Genetic and rare diseases (Type I collagenopathy, SERPINH1, CREB3L1 mutations); and Osteoarthritis (OA), which includes most common type of arthritis. Disease related to impaired Unfolding Protein Response (UPR) include: Ichthyosis follicularis with alopecia and photophobia (IFAP) syndrome.

A nucleic acid that corrects a mutation in the MBTPS1 gene or protein refers to a composition comprising an oligonucleotide that corrects a mutation in the coding sequence of the MBTPS1 gene, a mutation in non-coding portions of the MBTPS1 gene (e.g., causes defects in splicing or control of expression, such as affecting the promoter, inducing or repressing sequences), or even an oligonucleotide that corrects the MBTPS1 gene, e.g., a sense or antisense oligonucleotide that corrects the MBTPS1 gene, which can be a morpholino oligonucleotide that corrects the MBTPS1 gene.

Experimental design. The study design was centered on the functional characterization of the pathogenic variants in MBTPS1 in the patient identified. These include in vitro and in vivo approaches to determine how the MBTPS1 pathogenic variants causes S1P deficiency as well as how S1P deficiency results in skeletal dysplasia in the patient. Patient fibroblasts, fibroblast-derived iPSCs, and mouse models were used in this study.

Cell culture. Primary fibroblasts from ML-II/IIa patients were purchased from Coriell Cell Repositories (GM02013/ML-II, GM00113/ML-IIIa). Saos2, a human osteosarcoma cell line purchased from the ATCC collection, was grown in McCoy's 5A supplemented with 15% FES, 100 U/ml penicillin, and 100 µg/ml streptomycin. Human primary fibroblasts were isolated from patient tissue samples and immortalized by human telomerase reverse transcriptase gene through lentiviral infection. Fibroblasts were cultured in DMEM supplemented with 10% FBS, 100 U/ml penicillin, and 100 µg/ml streptomycin. Epstein-Barr virus-transformed (EBV-transformed) human immortalized B cells were grown in RPMI1640 supplemented with 10% FBS, 100 U/ml penicillin, and 100 µg/ml streptomycin.

Measurement of lysosomal enzyme activities. A fixed volume of plasma from mice and human or culture supernatant from Saos2 cells was incubated with an enzyme-specific 4-methylumbelliferone-conjugated (4-MU-conjugated) substrate for a specified length of time (27). The fluorescence released during the enzymatic reaction was measured using a FLUO-star Omega microplate reader (BMG Labtech). As a positive control for β-hexosaminidase activity in the supernatant of cultured cells, ionomycin was used to stimulate suspended Saos2 cells for 10 minutes. After centrifugation with 500 g for 3 minutes, supernatant from Saos2 cells was collected for the assay.

Prediction of the catalytic domain structure of human S1P. The predicted catalytic domain of human S1P was built using homology-based modeling in SWISS-MODEL (https://swissmodel.expasy.org/). The molecular visualization system PyMOL (open-source software published by DeLano Scientific was used to depict the structures.

Genetic mutation analysis in this family. Direct sequencing of PCR amplicons from genomic DNA extracted from EBV-mediated immortalized human B cells was performed to confirm germline mutation of MBTPS1 using an ABI 3730 capillary sequencer (Applied Biosystems). The sequences were analyzed using MacVector software (MacVector Inc.). For analysis of alternative splicing, PCR amplicons containing exon 9 from cDNA synthesized from patient-derived immortalized B cells were subcloned into pcDNA3.1(+), and then individual clones were sequenced.

Gene expression analyses with qPCR. Gene expression levels in the patient and irrelevant healthy control immortalized B cells or immortalized fibroblasts were analyzed by qPCR using primers listed in Supplemental Table 3. Total RNA extracted from the cells using Trizol was converted to cDNA using the M-MLV Reverse Transcriptase system. PCR analysis of cDNA was performed with the SYBR Green qPCR system using a CFX96 Real-time system instrument (Bio-Rad). To test for NMD, treatment with cycloheximide (100 µM) was performed by incubating patient's parental immortalized B cells for 6 hours, and then transcripts were analyzed by direct sequencing.

Plasmids. The C-terminal myc-FLAG-tagged human S1P in the expression vector pCMV6 was purchased from OriGene. S414A- and D365G-carrying S1P expression vectors and R925A-carrying a GPT α/β subunit precursor were generated by site-directed mutagenesis. A truncated α/β subunit precursor lacking amino acids 431-819, designated as myc3-tagged GPT reporter, was generated using the original GPT α/β-subunit precursor tagged with C-terminal myc3 as a template for inverse PCR (4). C-terminal myc3-tagged BBF2H7 was subcloned into pcDNA3.1(+). C-terminal myc-FLAG-tagged human S1P, C-terminal myc3-tagged α/β subunit precursor, and C-terminal myc3 tagged BBF2H7 p60 (residue 1-377 amino acids) were sub-cloned into pHIV-ZsGreen for lentivirus transduction system (18) (a gift from Bryant Welm, University of Utah, Salt Lake City, Utah, USA).

TABLE 1

The following primers were used in this study.

| | |
|---|---|
| Hprt: forward primer,<br>5'-CCTGCTGGATTACATCAAAGCACTG-3' | SEQ ID NO: 2 |
| reverse primer,<br>5'-GTCAAGGGCATATCCTACAACAAAC-3' | SEQ ID NO: 3 |
| Mbtps1: forward primer,<br>5'-TCCAATTGCTTGGATGACAG-3' | SEQ ID NO: 4 |
| reverse primer,<br>5'-TCCAGAACCTTGGAGTACCG-3' | SEQ ID NO: 5 |
| Dhcr7: forward primer,<br>5'-ACGCTGCAGGGTCTGTACTT-3' | SEQ ID NO: 6 |
| reverse primer,<br>5'-ACAGGTCCTTCTGGTGGTTG-3' | SEQ ID NO: 7 |

TABLE 1-continued

The following primers were used in this study.

| | |
|---|---|
| Sec23a: forward primer,<br>5'-ACCAAAGACATGCATGGACA-3' | SEQ ID NO: 8 |
| reverse primer,<br>5'-CACAAACTGGATTGCACCAC-3' | SEQ ID NO: 9 |
| Col1a1: forward primer,<br>5'-AGCCAGCAGATCGAGAACAT-3' | SEQ ID NO: 10 |
| reverse primer,<br>5'-TCTTGTCCTTGGGGTTCTTG-3' | SEQ ID NO: 11 |
| Hspa5: forward primer,<br>5'-TAGCGTATGGTGCTGCTGTC-3' | SEQ ID NO: 12 |
| reverse primer,<br>5'-TTTGTCAGGGGTCTTTCACC-3' | SEQ ID NO: 13 |
| Ddit3: forward primer,<br>5'-CAGAACCAGCAGAGGTCACA-3' | SEQ ID NO: 14 |
| reverse primer,<br>5'-TCACCATTCGGTCAATCAGA-3' | SEQ ID NO: 15 |
| Runx2: forward primer,<br>5'-GACGAGGCAAGAGTTTCACC-3' | SEQ ID NO: 16 |
| reverse primer,<br>5'-GCCTGGGGTCTGTAATCTGA-3' | SEQ ID NO: 17 |
| Col2a1: forward primer,<br>5'-CAGTTGGGAGTAATGCAAG-3' | SEQ ID NO: 18 |
| reverse primer,<br>5'-GCCTGGATAACCTCTGTG-3' | SEQ ID NO: 19 |
| Col10a1: forward primer,<br>5'-AGGAATGCCTGTGTCTGCTT-3' | SEQ ID NO: 20 |
| reverse primer,<br>5'-ACAGGCCTACCCAAACATGA-3' | SEQ ID NO: 21 |
| Trappc2: forward primer,<br>5'-GGAAGGCAGAATCCAAAGACG-3' | SEQ ID NO: 22 |
| reverse primer,<br>5'-ATGCCGACACAAACCACTCG-3' | SEQ ID NO: 23 |
| Mia3: forward primer,<br>5'-CCTTGAGGCAGAAAGTGGAG-3' | SEQ ID NO: 24 |
| reverse primer,<br>5'-CATGGGTAGCGATCTGGTTT-3' | SEQ ID NO: 25 |
| Serpinh1: forward primer,<br>5'-AGCAGCAAGCAGCACTACAA-3' | SEQ ID NO: 26 |
| reverse primer,<br>5'-AGGACCGAGTCACCATGAAG-3' | SEQ ID NO: 27 |

Transfection. CHO-7 and SRD-12B cells were transfected with myc3-tagged GPT reporter and with each S1P expression vector at a ratio of 100:1 using Fugene6 transfection reagent. After 48 hours, transfection efficiency was determined by EGFP expression with flow cytometry. Infection-competent lentivirus was generated from HEK293T cells transfected with expression vectors pLV-HELP and pMD2.G using PEImax transfection reagent (Polysciences Inc.). After 48 hours, lentivirus-containing culture supernatant was collected, and then cells of interest were infected and sorted based on ZsGreen expression.

Western blotting. Protein extracts from cultured cells or tissues were prepared using a 1% Triton X-100-based cell lysis buffer. Lysates were applied to an 8%-12% SDS-PAGE gel. Separated proteins were transferred onto an Immo-bilon-P membrane (Millipore). After blots were blocked, the membranes were incubated with antibodies and were then developed with ECL systems. Exposed X-ray films were scanned and analyzed with ImageJ software (NIH). For protein extraction from cartilage from mouse ribs, proteins from frozen tissues were extracted into 8 M urea lysis buffer using Bead-beater (34) (Biospec Products Inc.). For detecting endogenous GPT in immortalized B cells, $1.5 \times 10^7$ cells were suspended in hypotonic lysis buffer and then ultrasonicated for 30 seconds. After removing debris by spinning at 1,000 g for 3 minutes, supernatant was further ultracentrifuged at 100,000 g for 2 hours. The membrane fractions were solubilized with 3% Triton X-100-containing lysis buffer, 150 µg protein was analyzed by Western blotting.

Immunoprecipitation. The supernatants collected from Saos2 cells cultured in serum-free conditions for 2 days were concentrated 10-fold using Amicon filters, mixed with SDS (final concentration of 2.86%), and then boiled for 5 minutes. After a 10-fold dilution with RIPA buffer, goat anti-cathepsin D (4 µg) and protein-G beads were added for the immunoprecipitation. Immunoprecipitates were eluted with SDS sample buffer and were then analyzed with a nonreducing SDS/PAGE gel. Trichloroacetic acid (TCA)/acetone precipitation was performed to prepare the input positive control. Briefly, 100 µl 100% TCA was added to 900 µl culture medium, and the sample was then incubated for 1 hour on ice. After centrifugation at 15,000 g for 20 minutes, pellets were washed once with cold acetone (Fisher Scientific). Finally, dried washed pellets were solubilized in 1×SDS sample buffer using ultrasonication.

CRISPR/Cas9. S1P-KO. GPT-KO, and S2P-KO cells were generated with CRISPR/Cas9 technology. Briefly, sgRNA oligonucleotides targeting the coding region of individual genes were designed using CHOPCHOP (http://chopchop.cbu.uib.no) and were subcloned into the Bbs1 site of the CRISPR plasmid pSpCas9 (BB)-2A-GFP (Addgene, plasmid 48138) (15). After transfection into Saos2 and HEK293T cells, GFP-positive cells were sorted into a 96-well plate at a density of 1 cell per well with a MoFLO cell sorter (Beckman Coulter). After the colonies had expanded to 50% confluency, the genomic DNA was extracted to perform genotyping PCR followed by direct DNA sequencing. Once S1P-KO clones were established based on genotyping, a cholesterol auxotrophy assay for survival and a reporter assay based on transfecting myc3-tagged GPT reporter were performed to confirm S1P deficiency (3, 35). Established S1P-KO and S2P-KO clones were confirmed to be cholesterol auxotrophic. Briefly, cells were cultured in serum-free OPTI-MEM1 medium with or without 50 µM sodium mevalonate. 20 µM sodium oleate, 5 µg/ml cholesterol, and 1% fatty acid-free BSA for 3 days followed by staining with crystal violet. GPT deficiency was validated by Western blotting of the membrane fraction using an anti-α subunit specific antibody (catalog sc-107561, Santa Cruz Biotech).

Generation of iPSCs. Primary skin fibroblasts derived from the patient and her parents were transfected with the Human iPS Cell Reprogramming Episomal Plasmid (AL-STEM) (36) according to the manufacturer's protocol using a Nucleofector II instrument (Lonza). The single colonies were isolated, expanded, and then validated as iPSCs by staining with antibodies against SSEA4 (catalog MC-813-70, STEMCELL Technologies) and TRA-1-60 (catalog TRA-1-60R, STEMCELL Technologies). Immunofluorescence. Cells plated on a glass coverslip were treated with 10 ng/ml TGF-β1 (Peprotech), 5-10 µM PF-429242, or 10 mM PBA for 48 hours. Then, cells were fixed with cold 100% methanol (Fisher Scientific) for 5 minutes at −20° C. After blocking with 1% BSA in PBS-T, the cells were incubated with primary antibodies for 2 hours and then with fluorescence-conjugated secondary antibodies for 1 hour. Counterstaining was performed using DAPI or TO-PRO3. Tissue sections were incubated with primary antibodies overnight at 4° C. Secondary antibodies were added for 1 hour at room temperature (37). Primary antibodies were against cathepsin D (catalog sc-6488), cathepsin B (catalog sc-13985), calnexin (catalog sc-23954), Sec31a (catalog sc-376587), Hsp47 (catalog sc-5293), FLAG (catalog sc-166355), myc (catalog sc-789) and BBF2H7 (catalog sc-69372, Santa Cruz Biotech); LANP1 (catalog 328602, Biolegend); collagen-II (catalog MA5-13026, Thermo Fisher Scientific); calnexin (catalog GTX109669) and Sec23a (catalog GTX109488, GeneTex Inc.); Tango1 (catalog HPA055922, MilliporeSigma); and collagen I (catalog ab34710) and collagen X (catalog ab58632, Abcam). Secondary antibodies were conjugated with DyLight 488, Alexa Fluor 555, or DyLight 649 (Jackson ImmunoResearch). The TUNEL-positive apoptotic cells were stained using the In Situ Cell Death Detection Kit, Fluorescein (MilliporeSigma). Samples were analyzed by confocal laser scanning microscopy using a Nikon C1 scanning head mounted on a Nikon ECLIPSE 200015 inverted microscope (Plan Apochromat dry objective lens, ×20, NA 0.75; Nikon Instruments Inc.) or a superresolution microscope (DeltaVision, OMX-SR).

Microscopy. For histology, femurs and brains from mice and human teratomas were fixed in 4% paraformaldehyde overnight at 4° C. and were then washed and embedded in paraffin. Sections (5 μm) were cut using a microtome and then stained with H&E. For confocal microscopy of cryosections, human teratomas were fixed in 4% paraformaldehyde overnight at 4° C., washed in PBS, cryoprotected in 20% sucrose in PBS at 4° C. overnight, embedded in 50% tissue freezing medium/50% OCT and cryosectioned (20- to 30-μm sections).

In vitro differentiation of osteoblasts from human iPSCs. Maternal and patient-derived iPSCs were seeded onto Matrigel-coated 6-well plates in the presence of Y-27632 (Cayman Chemical) and incubated at 37° C. in a 5% $CO_2$ incubator. The next day, mTeSR1 medium was replaced with fresh 10% FBS-containing D-MEM medium supplemented with 50 μg/ml ascorbic acid, 10 mM β-glycerophosphate (Santa Cruz Biotech), and 100 nM dexamethasone. This osteogenic medium was changed every day without harvesting and reseeding. After 2 weeks, the cells were either stained with Alizarin Red S or the RNA was extracted for qRT-PCR (17).

AMO. The AMO (5'-AGAAAAGCGGGCGATGT-TAcCTTCA-3' [the lowercase "c" represents the mutated base compared to healthy control]) against exon 9 in the maternal mutant transcript containing cryptic splice donor site was designed (Gene Tools Inc.) (38). Forty thousand fibroblasts were seeded onto a 24-well plate. Introduction of AMO (10 μM) in maternal and patient fibroblasts was carried out using the Endo-Porter (6 μM) peptide delivery system (Gene Tools Inc.). After 12, 24, and 48 hours, RNA was extracted for quantitative RT-PCR as well as cloning of MBTPS1 cDNA. The following primer pair was used to quantify a MBTPS1 transcript with 41-bp deletion in exon 9: forward primer targeting the boundary exons 7 and 8, 5'-CCGTTTGTTGACAAGGTGTG-3'; reverse primer targeting exon 10, 5'-CTGG-TAGCTCCTTCAAAGTC-3'.

Measurement of secreted procollagen I. Supernatant from cultured fibroblasts was collected at 48 hours after treatment with AMO and was then diluted 500-fold with PBS (39). Secreted procollagen 1a in diluted samples was measured with an ELISA kit according to the manufacturer's instructions (R&D Systems).

Other reagents. MU N-acetyl-β-D-glucosaminide, cycloheximide, trichloroacetic acid, PBA, BSA, mevalonate, oleate, cholesterol, fatty acid-free BSA, crystal violet, alizarin red S, ascorbic acid, and dexamethasone were purchased from MilliporeSigma. Trizol and protein G magnetic Dynabeads were purchased from Invitrogen. The M-MLV Reverse Transcriptase system. ECL systems, DAPI, and TO-PRO3 were purchased from Thermo Fisher Scientific. The SYBR Green qPCR system was purchased from Bio-Rad. Fugene6 transfection reagent was purchased from Promega. A myc-His-tagged, single-chain variable fragment (scFv) against M6P residues (scFv M6P-1) was purchased from Ascenion GmbH.

Animal models. Teratoma for nation assay. Human iPSCs derived from the patient and her parents were grown to near confluence, treated with Accutase (STEMCELL Technologies), harvested in PBS, and then resuspended in 30% Matrigel-containing DMEM-F12 (Corning). Immune-deficient NRG mice (either sex, 6-8 weeks of age) were anesthetized and then subcutaneously injected with approximately $1 \times 10^6$ to $5 \times 10^6$ cells in 200 μl/injection site. Mice were injected in the dorsolateral area into the subcutaneous space on both sides. After 7-10 weeks, mice were euthanized by $CO_2$ exposure, and then the teratomas were dissected.

S1P-deficient mice. To generate mice with global inducible deletion of S1P (Mbtps1f/f;CagCreERTM), Mbtps1f/f mice (provided by Jay Horton, University of Texas Southwestern Medical Center, Dallas, Texas USA) (7) were crossed with the CagCreERTM-transgenic mice (B6.Cg-Tg (CAG-cre/Esr1*)5Amc/J, Jackson Laboratories). To induce postnatal deletion of S1P, tamoxifen (MP Biomedicals) was dissolved in ethanol/sunflower oil (1:9) and administered orally (p.o.) (20 μg per day) to pups from P1 to P7. Adult deletion was accomplished by administering tamoxifen p.o. (500 μg per day) every other day for 4 times. WT littermates (Mbtps1f/w;CagCre or Mbtps1f/f) treated with the same regimen were used as controls. Mice deficient for S1P in chondrocytes (Mbtps1f/f;Col2a1CreERT2) were generated by crossing Mbtps1f/f mice with Col2a1CreERT2-transgenic mice. All mice were maintained on a C57BL/6J background. Mice were bred and maintained in specific pathogen-free AAALAC-accredited animal facilities. Both sexes (6-12 weeks of age) were used for experiments. Mice were genotyped routinely by PCR assay on genomic DNA isolated from tail clips.

Statistics. Statistical tests were performed using Prism software (GraphPad). Two-sided, two-tailed Student's t tests were performed to assess the statistical significance of differences between 2 groups after the data were confirmed to fulfill the criteria of normal distribution and equal variance. One-way analysis of variance was used to analyze the significance of differences among 3 or more groups. Differences were considered statistically significant at $P<0.05$.

Patient Information. Patient is currently 11½ years of age. She was born following an uncomplicated pregnancy to her G3P2 mother and father. Birth weight at term was 2.07 kg, and was considered small for gestational age at birth. At birth, no other concerns were identified. Up to 6 mo of age, her length and weight were at 5%, after which gain in weight and height slowed down considerably. At 2 years of age she had bilateral cataract extraction, identified a few months earlier.

Attainment of gross motor milestones was delayed, but speech and cognitive development were rather normal. At age 3 years, she was seen in pediatric endocrinology clinic, and thought to have Russell-Silver syndrome, but no molecular testing was pursued Human growth hormone replacement therapy was started, but discontinued after 1 year due to limited response. She had elective bilateral inguinal hernia repair at age 3½ years. At age 6 years, she was referred to pediatric orthopedics for back pain. Other than the short stature, she was thought to have unusual face. Short stature was again observed, and other skeletal findings were pectus carinatum, kyphosis, and waddling gait. Radiology done at that time revealed spondyloepiphyseal dysplasia, with associated kyphosis. She was referred to Medical Genetics. A SNP array revealed a heterozygous duplication on chr19q13.42 (genomic coordinates: chr19: 54,659,105-55,909,948 x3, hg19), determined to be maternally inherited, and therefore assessed as a likely harmless copy number variant. COL2A1 (MIM 120140) sequencing was performed and found to be normal. At age 8, she was found to have markedly elevated plasma levels of various lysosomal enzymes (beta-galactosidase, beta-mannosidase, alpha-mannosidase, beta-glucuronidase, alpha-glucosaminidase, and beta-hexosaminidase were all elevated), which was confirmed on repeat testing, while urinary glycosaminoglycans were normal. Deficient activity of UDP-N-acetylglucosamine:lysosomal-enzyme N-acetylglucosamine-1-phosphotransferase (GlcNAc-phosphotransferase; EC 2.7.8.17) was suspected. However, Sanger sequencing and deletion/duplication testing of GNPTAB (MIM 607840) and GNPTG (MIM 607838) revealed only a heterozygous c.2499A>G, (p.E833F) in GNPTAB. At age 9, a complete metabolic panel (incl. alkaline phosphatase) was normal, also serum Calcium, and intact parathyroid hormone. At age 10 years, complete blood count was normal, and biochemical studies done as part of bone health evaluation revealed normal bone-specific alkaline phosphatase 56.4 ug/L (nl 47.9-150.8), elevated serum N-telopeptide 44.4 (nl 6.2-19.0), elevated urine N-telopeptide/creatinine 907 (nl Tanner Stage I Female 6-662), and elevated osteocalcin 58.0 ng/mL (nl in pre-menopausal women: 4.9-30.9). DXA scan reveals z-score of −4.5 at TBLH, and z-score of −3.3 at AP spine.

Even after correcting for her significant short stature, this is low. Vitamin D studies were normal. Echocardiogram at age 10½ yrs was normal. Radiographs done at 11½ yrs of age revealed stable complete anterolisthesis of L5 on S1, bilateral shortening of the femoral necks with irregular and dysplastic appearance of the femoral and proximal tibial epiphyses. Fibula are gracile with valgus bowing. Bone age revealed concordance of chronological age and skeletal age. She continues was dysmorphic facial features, with prominent forehead, prominent cheekbones, large ears, with unusual distribution of subcutaneous fat, suggestive of possible lipodystrophy.

TABLE 2

Age, Weight and Height measurements.

| Age | Weight (kg) | Length/Height (cm) |
|---|---|---|
| 0 mo | 2.07 | 44.5 |
| 6 mo | 5.44 | 57.2 |
| 9 mo | 5.67 | 61.6 |
| 12 mo | 6.49 | 65.0 |
| 24 mo | 7.88 | 76.5 |
| 36 mo | 8.73 | 79.4 |
| 7½ yrs | 12.1 | 95.8 |
| 11½ yrs | 15.9 | 109.7 |

Table 3. Comparison of the MBTPS1 mutation-caused syndrome with ML-II/III, IFAP syndrome, and Serpin H1 deficiency. Mucolipidosis-II/III caused by genetic mutation in GNPTAB causes bone dysplasia due to massive bone absorption and defective lysosomal functions. Some patients with ichthyosis follicularis, alopecia, and photophobia (IFAP) syndrome caused by genetic mutation in MBTPS2, which encodes site-2 protease (S2P) and cleave substrates after S1P-mediated cleavage, show bone dysplasia possibly caused by defective ER functions involving improper protein folding and extracellular secretion. Serpin H1 deficiency results in abnormal transporting of large molecules such as collagen from ER to Golgi. By contrast, the patient in this study with genetic mutations in MBTPS1 shows bone dysplasia by compound defects of lysosomes and ER.

TABLE 3

Comparison of the MBTPS1 mutation-caused syndrome with ML- II/III, IFAP syndrome, and Serpin H1 deficiency.

|  | S1P deficiency | Mucolipidosis II/III | IFAP syndrome | Serpin H1 deficiency |
|---|---|---|---|---|
| Mutated gene | MBTPS1 | GNPTAB | MBTPS2 | HSP47 |
| Affected protein | S1P | GPT | S2P | Serpin H1 |
| Reduced cognition | no | yes | n/a | n/a |
| Growth | yes | yes | yes | yes |
| Cataract | yes | no | n/a | n/a |
| Visual (photophobia) | no | no | yes | n/a |
| Blue sclerae | no | no | yes | yes |
| Alopecia | no | no | yes | ? |
| Ichthyosis follicularis | no | no | yes | yes |
| Aortic valve defects | no | yes | n/a | n/a |
| Inguinal hernia | yes | yes | n/a | yes |
| Bone dysplasia | yes | yes | yes | yes |
| Serum N- telopeptide | yes | yes | ? | no |
| Blood lipids | yes (modest) | no | n/a | n/a |
| Elevated blood lysosome enzymes | yes | yes | no | no |
| Affected organelle | lysosome and ER | lysosome | ER | ER |
| Cellular defects | defective function of lysosome and ER | defective function of lysosome | defective function of ER | defective function of ER |

Figure 1B:
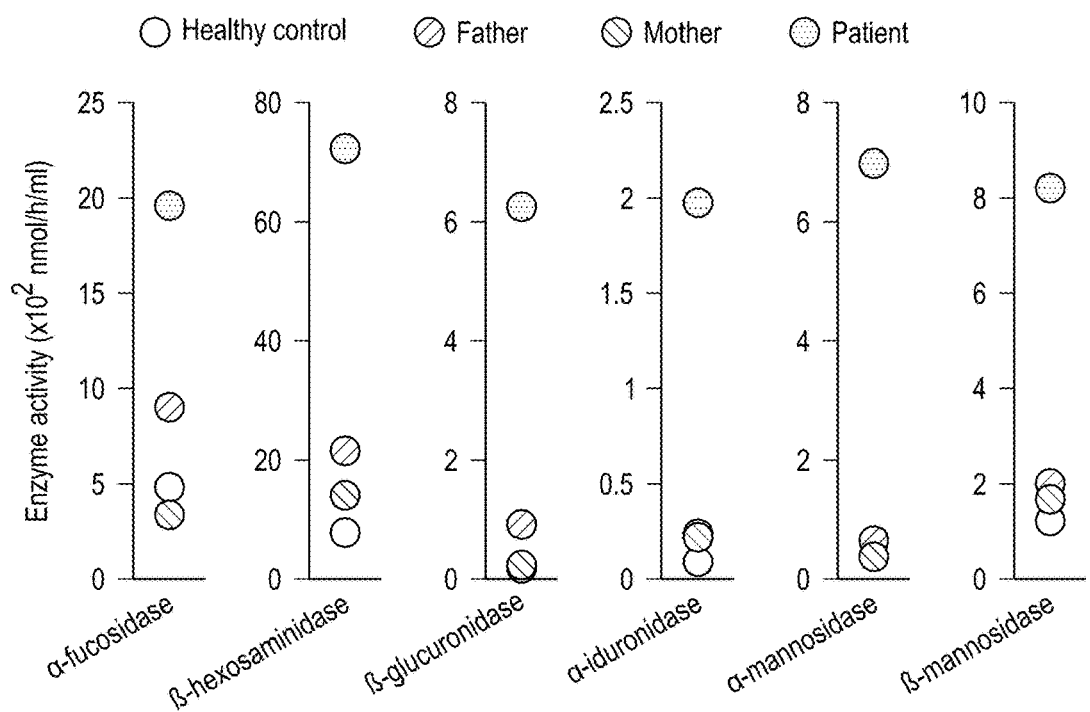

Unique amorphic and severely hypomorphic mutations in S1P gene were identified in a patient with skeletal dysplasia and elevated blood lysosomal enzymes. The patient was born with birth weight of 2.07 kg and no gross abnormalities. At 6 months of age, her length and weight were at 5% compared with healthy controls, after which growth in height and weight slowed down. At 2 years of age, attainment of gross motor milestones was delayed, but speech and cognitive development were normal. At 3 years of age, she was thought to have Russell-Silver syndrome and, therefore, growth hormone replacement therapy was started but discontinued after 1 year due to limited response. She had elective bilateral inguinal hernia repair at age 3.5 years. At 6 years of age, she had spondyloepiphyseal dysplasia with associated kyphosis as well as dysmorphic facial features, with prominent forehead, prominent cheekbones, and large ears (FIG. 1A). Her primary clinical presentations are retarded growth with skeletal abnormalities, including a bone mineral density of approximately 60% relative to healthy controls. At age 8 years, she was found to have normal serum chemistry, liver function, and blood cell counts but displayed markedly elevated plasma levels of lysosomal enzymes compared with those of her parents and a healthy control (FIG. 1B). Her parents and two sisters are healthy. Based on her clinical presentations and abnormal blood chemistry (FIGS. 1A and 1B), she was given a provisional diagnosis of mucolipidosis III (ML-III), a lysosomal storage disease that is caused by mutations in the genes GNPTAB or GNPTG that encode GPT subunits (11, 12). Of note, however, she lacked common features of ML-II/III (cognitive and hearing impairment or cardiac valvular defects) (4, 11-13).

Figure 1C:
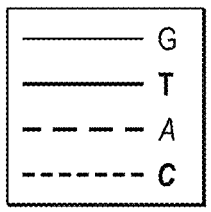
Figure 1C:
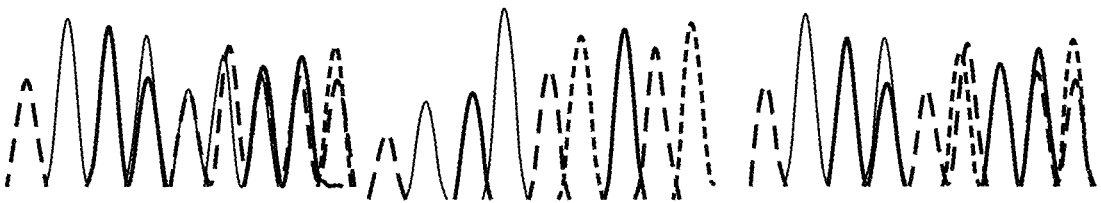
Figure 1C:
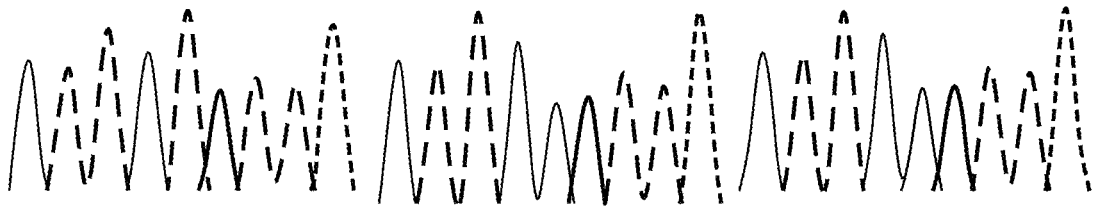

Unexpectedly, Sanger sequencing of GNPTAB and GNPTG did not reveal findings consistent with ML-II/III; instead, using whole-exome sequencing, biallelic variants in MBTPS1 were identified. The paternal variant was a nucleotide duplication (NM_003791.3: c.285dupT) in exon 3, predicted to create a nonsense change (p.D96X) (FIG. 1C). The maternal variant was a nucleotide substitution (NM_003791.3: c.1094A>G) in exon 9, predicted to result in a missense variant substituting aspartic acid for glycine (p.D365G) (FIG. 1C).

Figure 1D:
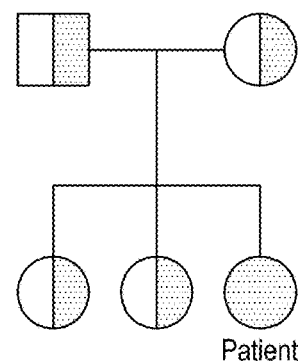
Figure 1E:
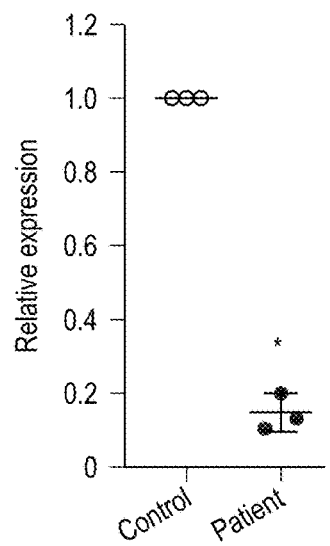
Figure 1F:
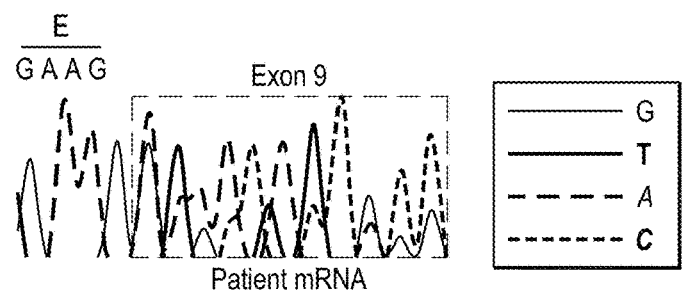
Figure 1G:
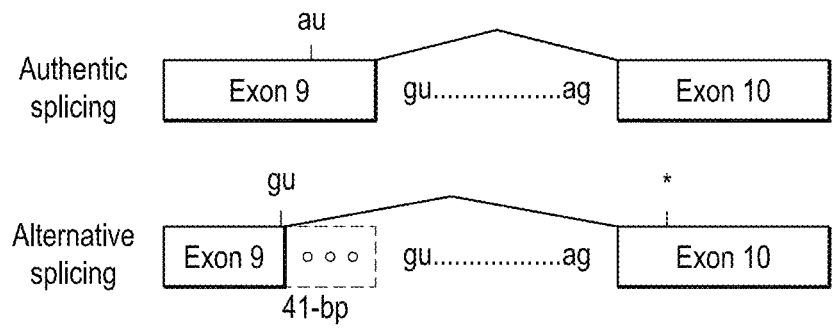
Figure 1H:
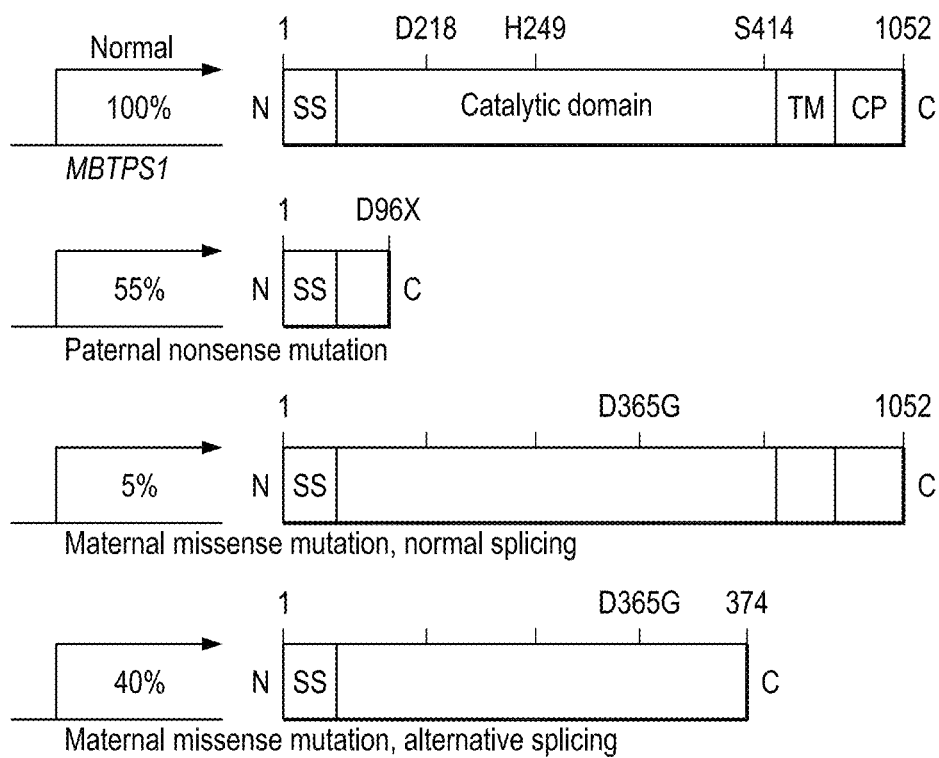
(FIG. 1H) Schematic domain of S1P in the patient. Green, catalytic triad; red, mutated residues. SS, signal sequence; TM, transmembrane domain; CP, cytoplasmic domain. The three different S1P variants are expressed in the patient.

The paternal variant (p.D96X) is expected to encode an S1P that lacks the entire catalytic domain (FIGS. 1D and 1H). The maternal variant (p.D365G) was not located within the S1P catalytic triad (FIGS. 1D and 1H), and in vitro site-directed mutagenesis of MBTPS1 cDNA with the maternal c.1094A>G variant indicated that S1P harboring the D365G (S1PD365G) had normal catalytic activity. However, qRT-PCR showed an 80% reduction of MBTPS1 expression in B cells from the patient compared with a normal control (FIG. 1E). To determine how the maternal c.1094A>G variant impairs MBTPS1 expression, the inventors individually cloned and sequenced RT-PCR amplicons from the patient MBTPS1 exons 7-10 and found that the maternal c.1094A>G variant created a dominant splice donor site in exon 9, resulting in an alternatively spliced transcript with a 41-bp deletion of exon 9, leading to a loss of S414 in the catalytic triad (FIGS. 1F and 1G). Treatment of parental B cells with a nonsense-mediated mRNA decay (NMD) inhibitor (cycloheximide) stabilized mutant MBTPS1 transcripts, indicating that this reduced MBTPS1 expression in the patient was caused by NMD (14). Together, the paternal and maternal variants generate only approximately 1% of the normally spliced, functional MBTPS1 (p.D365G) transcripts in the patient compared with healthy control.

Figure 2A:
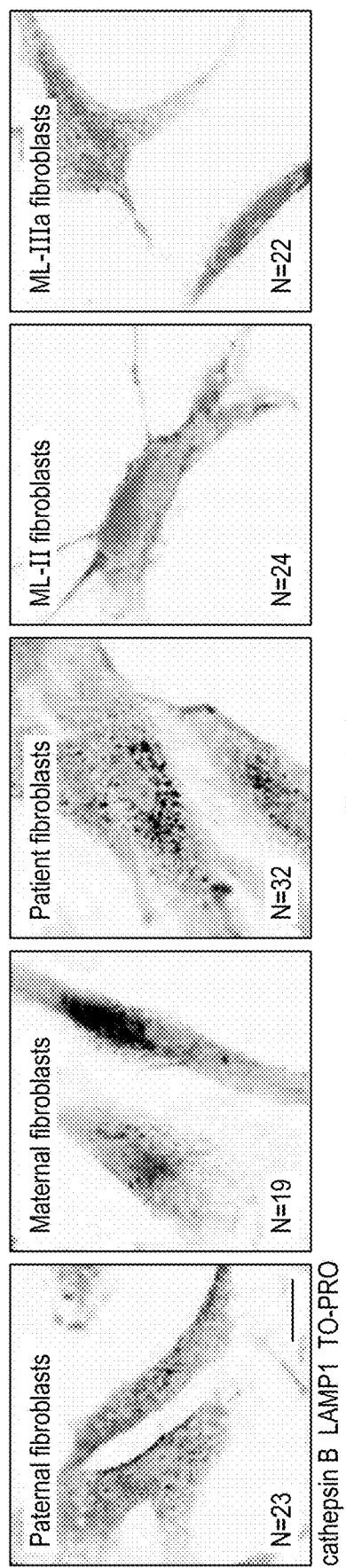
FIGS. 2A to 2G show that S1P deficiency causes a partially defective M6P-dependent Golgi-to-lysosome transport of lysosomal enzymes.
Figure 2B:
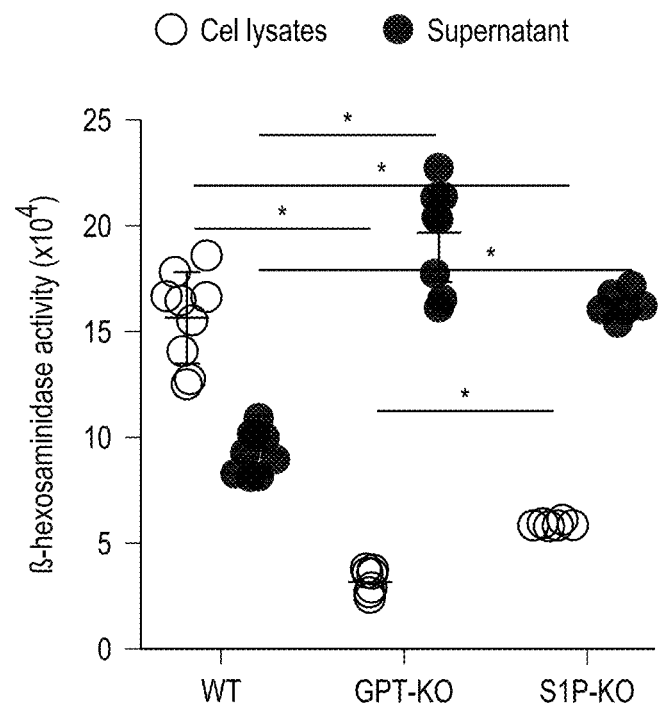
Figure 2C:
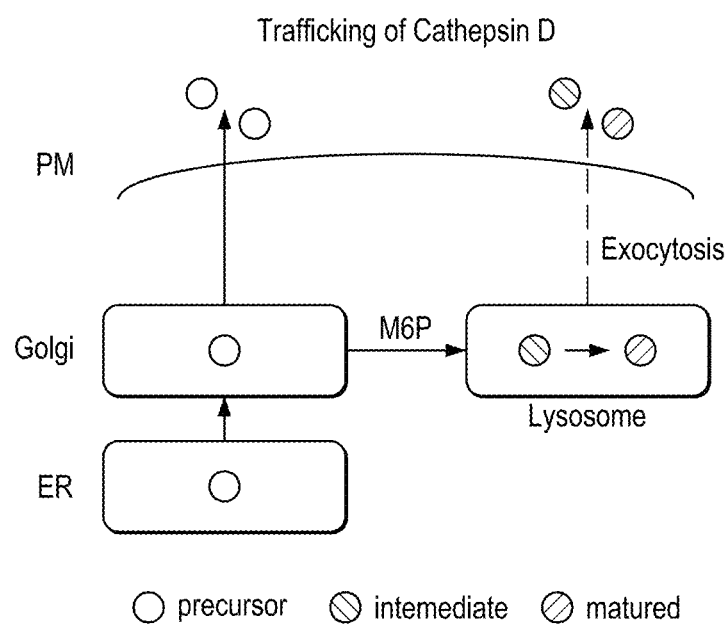
Figure 2D:
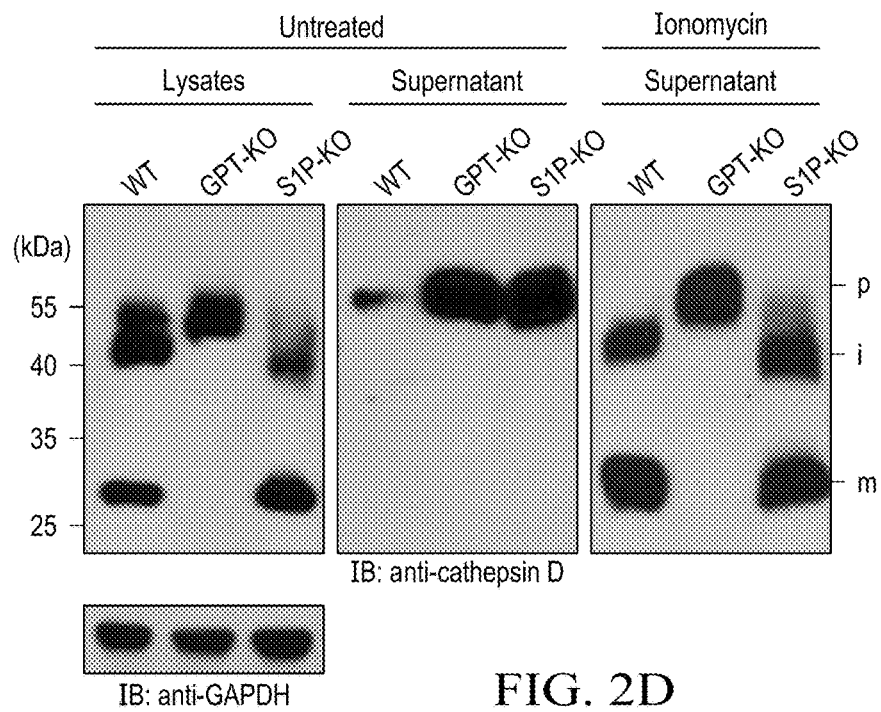
Figure 2E:
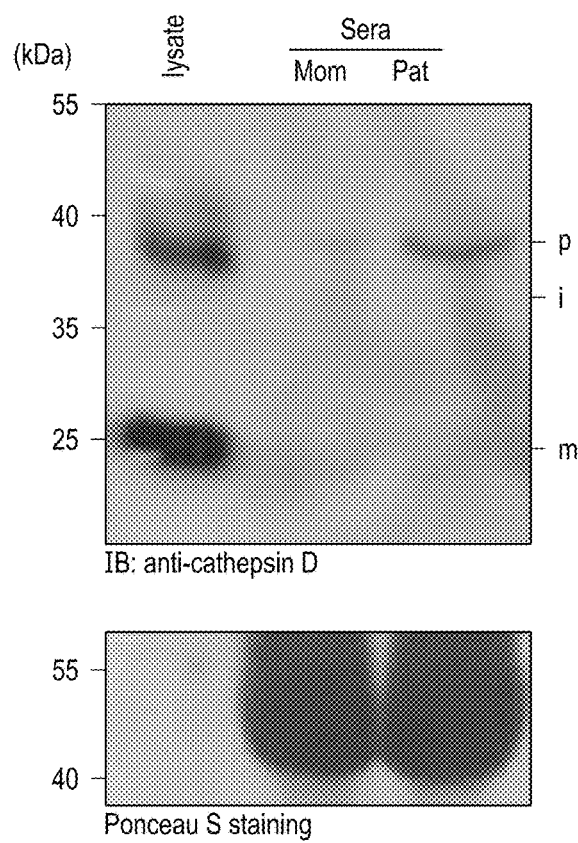
Figure 2F:
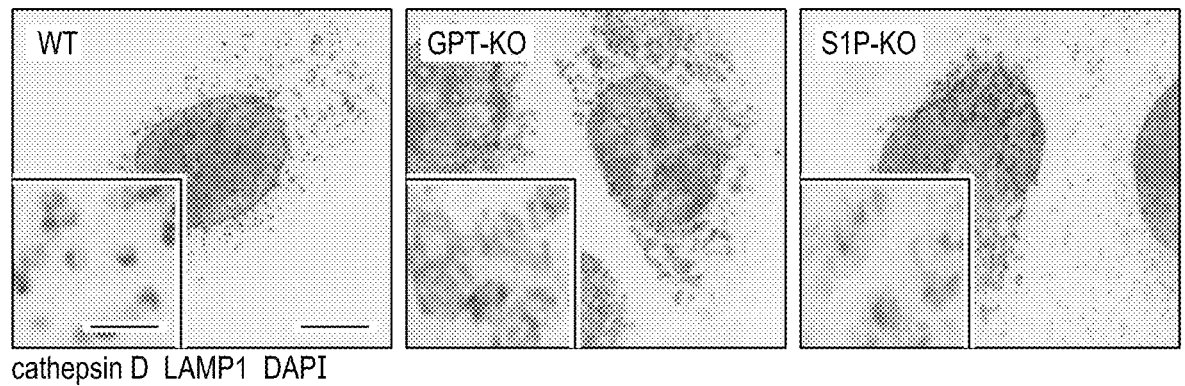
Figure 2G:
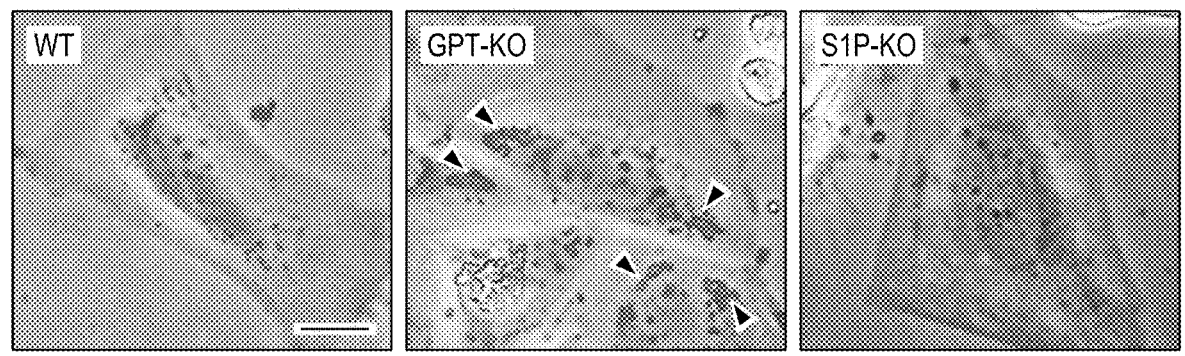
Figure 3A:
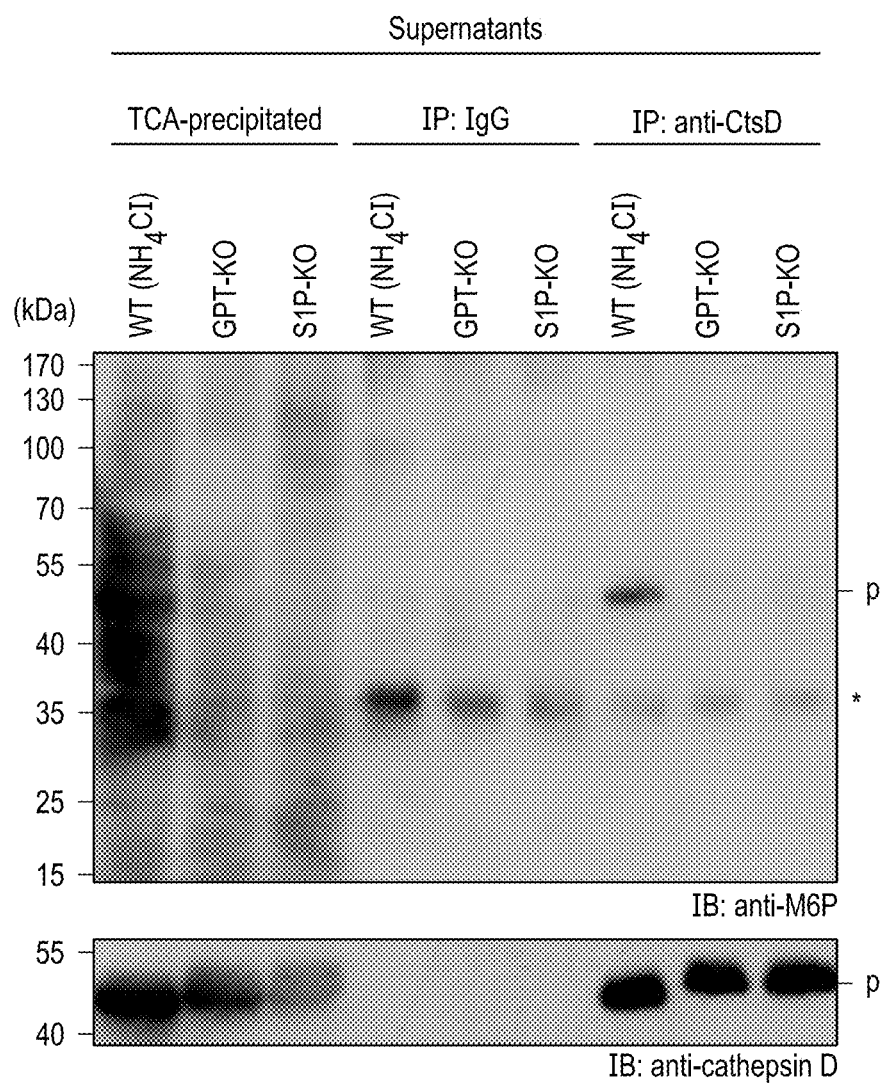
FIGS. 3A to 3G show that S1P is important but is not the sole enzyme that activates GPT.

S1P deficiency causes a partially defective M6P-dependent Golgi-to-lysosome transport of lysosomal enzymes. Previous in vitro studies indicate that S1P activates GPT by cleaving its α/β subunit precursor (4), which is required for the M6P modification of lysosomal enzymes in the Golgi apparatus for their targeted transport to the lysosome (5). Defective M6P modification causes the lysosomal storage diseases ML-II/III (6). Consistent with this, the patient exhibited elevated circulating lysosomal enzyme activities. The inventors evaluated patient fibroblasts for the lysosomal abnormalities typically observed in ML-II/III patient cells, such as inclusion bodies, enlarged lysosomes, increased levels of lysosomal proteins, and diffused distribution or increased secretion of lysosomal enzymes (11-13). Surprisingly, the inventors detected neither defective M6P modification nor any of the aforementioned lysosomal abnormalities in the patient fibroblasts (FIG. 2A). However, once the maternal and patient fibroblasts were treated with S1P inhibitor PF-429242, elevated secretion of lysosomal enzymes and lysosomal hypertrophy were found in both cells, indicating that residually expressed S1P is sufficient to maintain lysosomal function in patient fibroblasts. Given that the patient has skeletal dysplasia, the inventors reasoned that secretory cells, such as osteoblasts or chondrocytes, might be more susceptible than fibroblasts to decreased S1P expression. To test this, the inventors generated a Saos2 osteosarcoma cell line lacking S1P (S1P-KO cells) (15). Saos2 cells lacking GPT (GPT-KO cells) were generated as the positive control. Culture supernatants from S1P-KO and GPT-KO clones showed increased activity of the M6P-dependent lysosomal enzyme β-hexosaminidase compared with supernatants from WT cells, indicating that S1P functions in targeting lysosomal enzymes to lysosomes (FIG. 2B). Cathepsin D, which is synthesized as a precursor form, is one of the M6P-modified lysosomal enzymes. Once cathepsin D precursor was transported from the Golgi apparatus to the lysosome, it was processed into its mature form (FIG. 2C). Relative to WT cells, both S1P-KO and GPT-KO cells secreted high levels of the lysosomal enzyme cathepsin D precursor (55 kDa, FIG. 2D, middle), supporting a default secretory pathway. The precursor form of cathepsin D was also detected in patient sera but not in maternal sera (FIG. 2E). M6P-marked cathepsin D was detected in supernatants from WT cells treated with NH4Cl, which induces direct secretion of lysosomal enzymes from the Golgi apparatus, but not in untreated S1P-KO or GPT-KO cells (FIG. 3A). These data indicate that the excessive secretion of cathepsin D from S1P-KO cells is due to defective M6P modification as in GPT-KO cells.

Figure 3B:
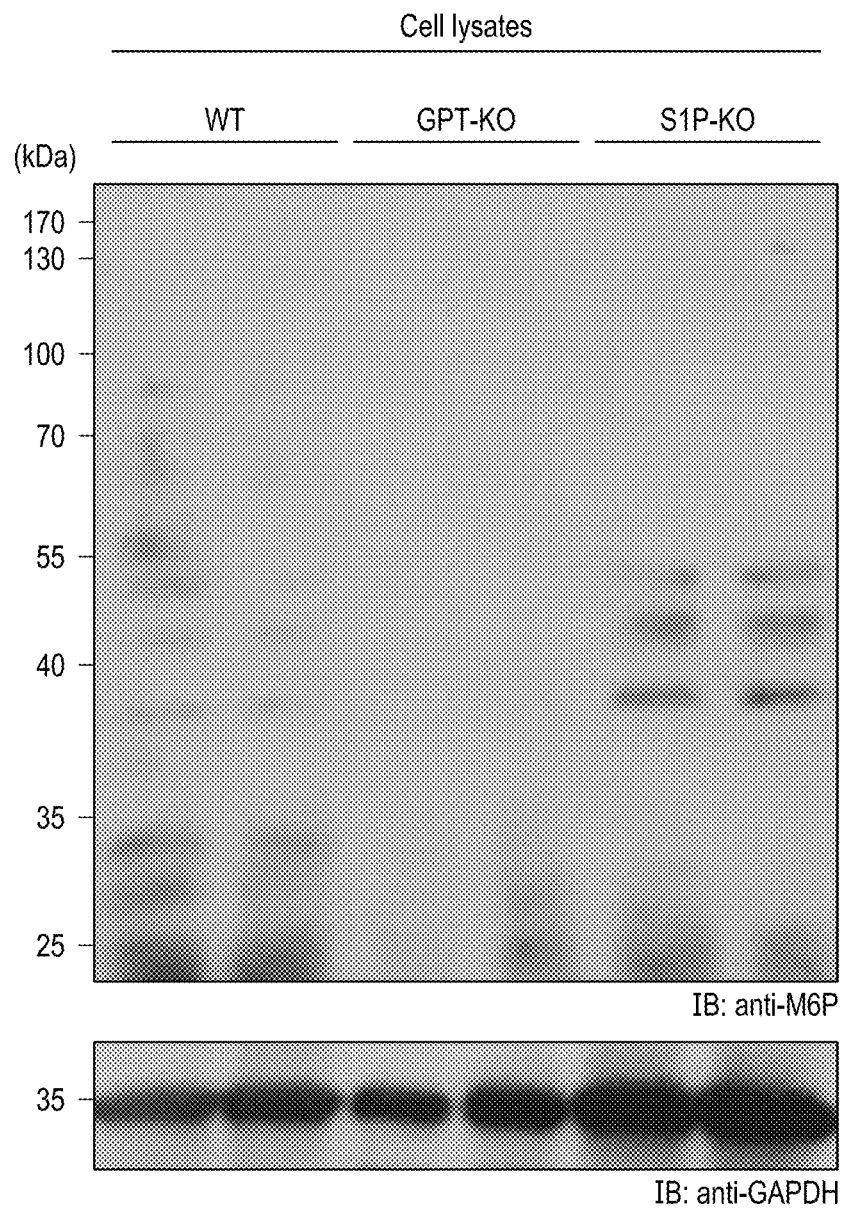
Figure 3C:
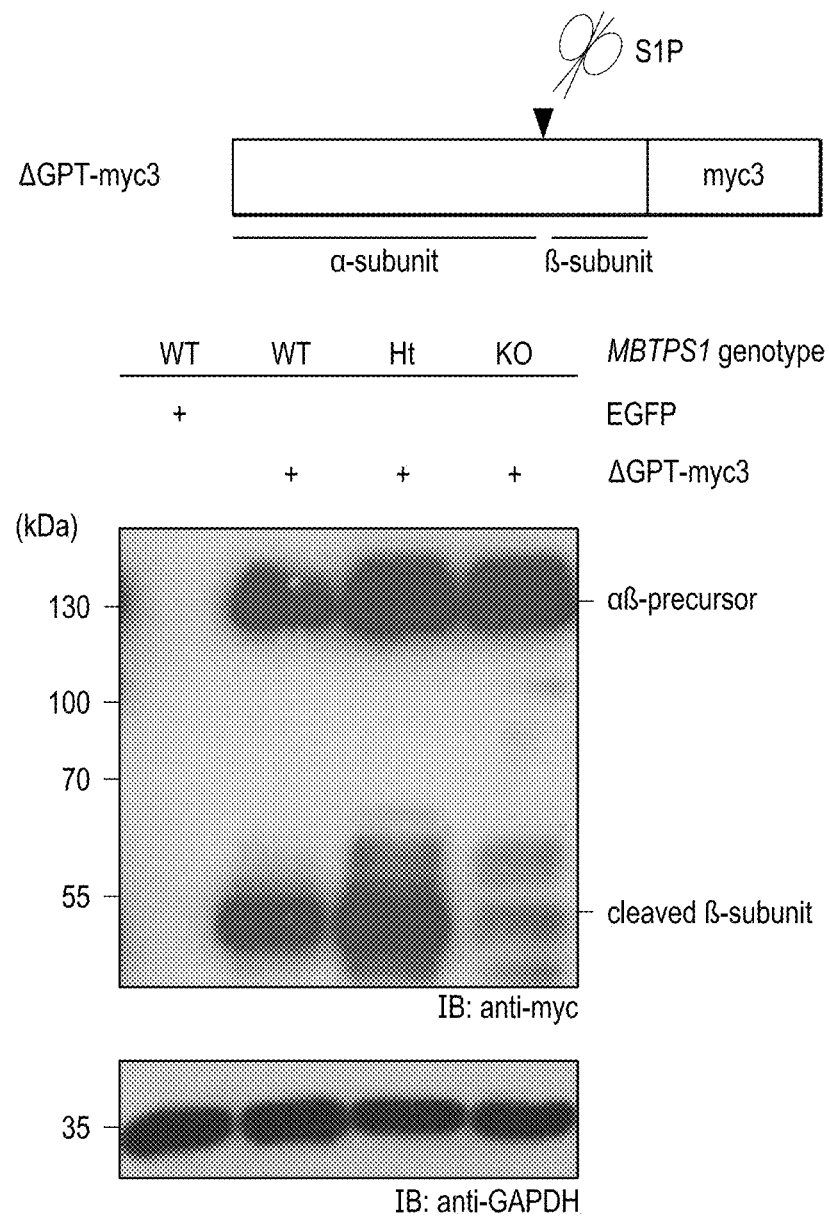
Figure 3D:
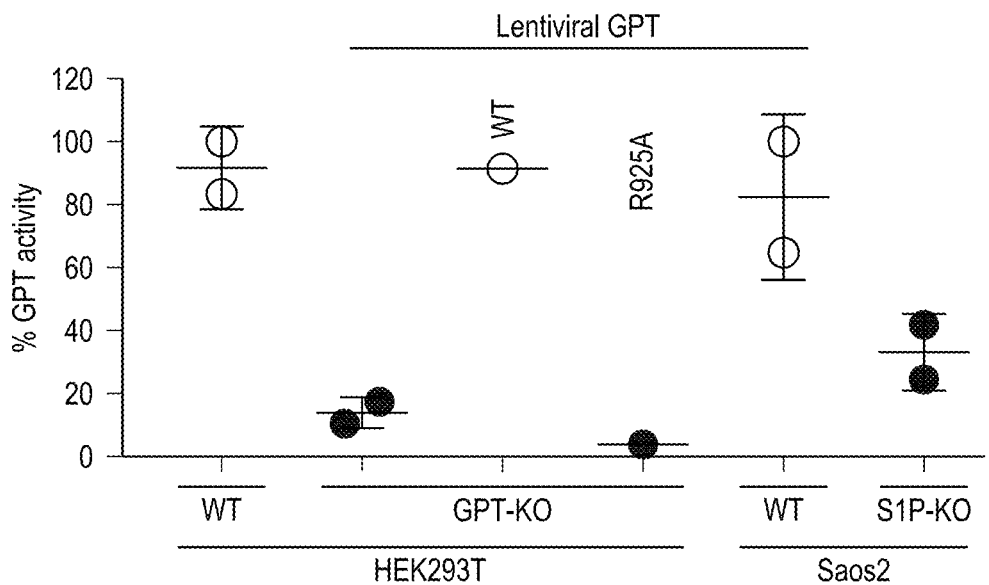

S1P is not the sole GPT-activating enzyme. Unexpectedly, the mature form (28 kDa) of cathepsin D was detected in the supernatant of S1P-KO cells but not in the supernatant of GPT-KO cells upon ionomycin-induced lysosomal exocytosis, indicating that cathepsin D was partially targeted to the lysosome in S1P-KO cells ure 2D, right). Further, S1P-KO cells had cathepsin D in lysosomes and did not have inclusion bodies, which is similar to WT cells (FIG. 2, F and G). In addition, the inventors found that M6P modified in lysates from S1P-KO cells was similar to that from WT cells (FIG. 3B), consistent with residual lysosomal targeting of M6P-dependent enzymes in S1P-KO cells. The inventors monitored cleavage of a myc3-tagged GPT reporter substrate, which is an artificial substrate of S1P, and observed some, albeit reduced, cleavage of myc3-tagged GPT reporter upon loss of S1P, suggesting an unknown S1P-independent mechanism for residual GPT activation (FIG. 3C). The inventors also measured GPT activity in those cells, and the inventors found that S1P-KO cells showed 30% activity compared with WT control cells (FIG. 3D). In summary, these data show that S1P-KO cells had less severe lysosomal phenotypes than in GPT-KO cells, indicating that S1P is important but not the sole enzyme to proteolytically activate GPT.

S1P regulates lysosomal enzyme trafficking in vivo, and chondrocytes are a major source of circulating lysosomal enzymes in the absence of S1P. To investigate the physiological requirements for S1P, the inventors analyzed mice with an inducible global (Mbtps1fl/fl;CagCreERTM) or chondrocyte-specific (Mbtps1fl/fl;Col2a1CreERT2) deficient of S1P (7, 10). Both mouse lines displayed elevated plasma lysosomal enzyme activities and bone defects, similar to the patient, whereas these phenotypes were not observed in their littermate controls. However, Mbtps1fl/fl; CagCreERTM mice, similar to the patient, did not have neurological defects, a common sign of ML-II/III, which also supports a S1P-independent mechanism for GPT activation, because GPT-deficient mice are reported to have inclusion bodies in neural cells (16). The elevated plasma lysosomal enzyme activities in Mbtps1fl/fl;Col2a1CreERT2 mice indicate that chondrocytes are a major source of circulating lysosomal enzymes.

The patient has no obvious metabolic abnormalities. In the Golgi membrane, S1P, acting sequentially with S2P encoded by MBTPS2, cleaves membrane-bound transcription factors in response to ER stress or decreased sterol metabolites. These substrates include SREBPs, which are critical for cholesterol biosynthesis, and ATF6, which is important for regulating ER stress responses (1, 7). These data show that the patient did not have any obvious metabolic abnormalities and her lipid levels were only slightly lower compared with controls under physiological conditions. Of note, the patient has a relatively low level of HDL, suggesting an important role of S1P in regulating HDL.

Figure 3E:
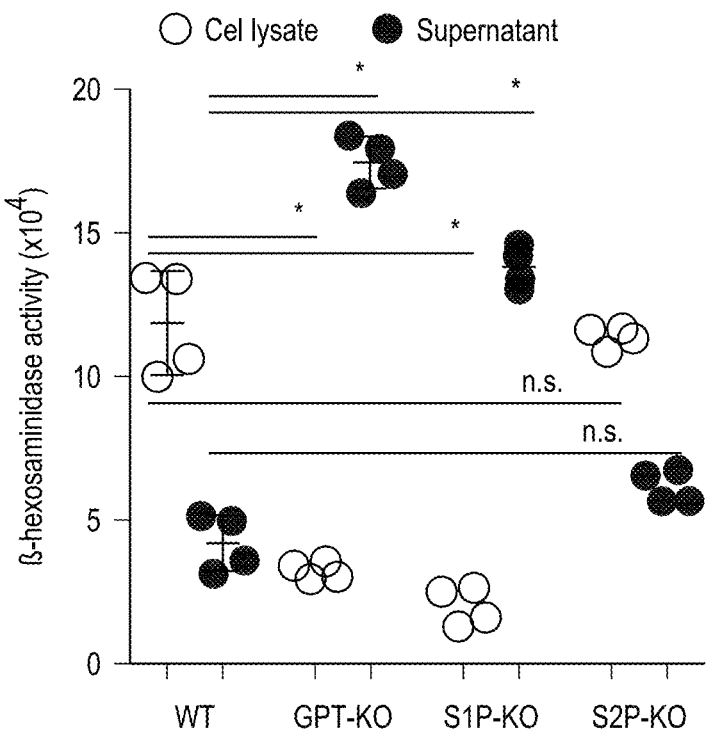
Figure 3F:
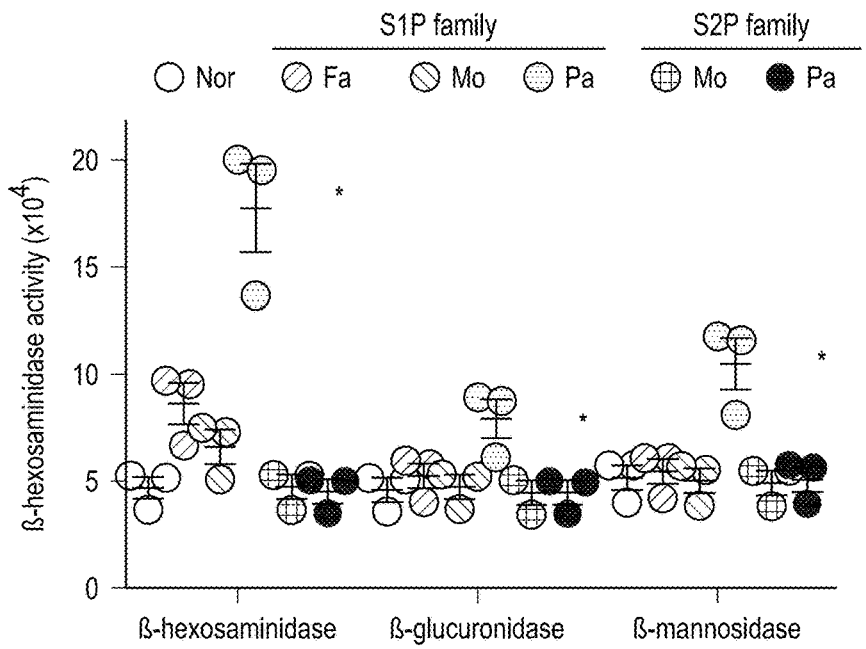
Figure 3G:
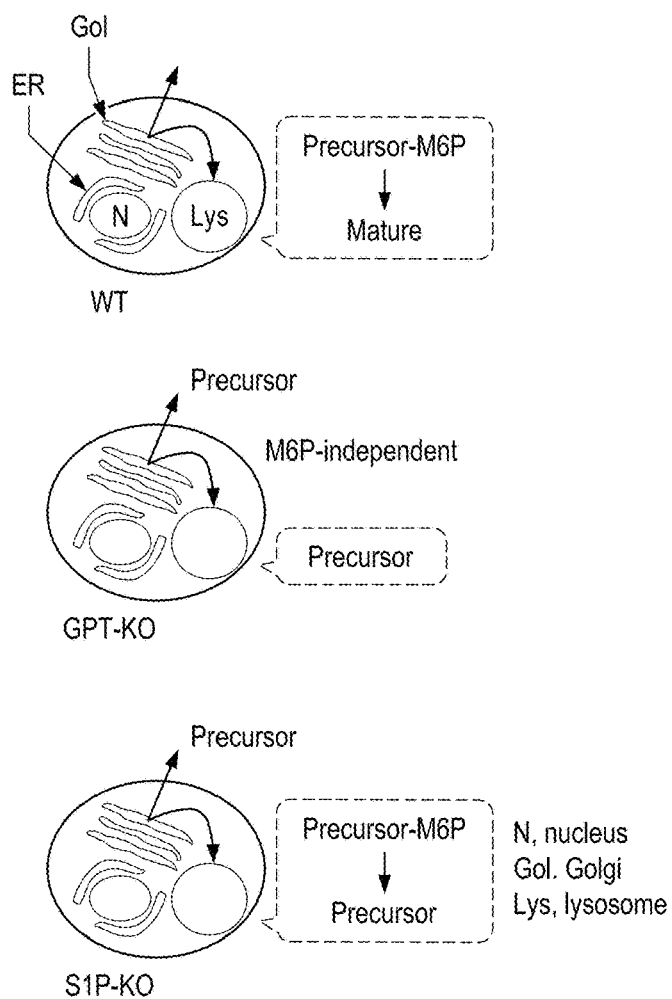

The present inventors also identified a patient with an S2P mutation. Both patient study and in vitro studies showed that the S2P pathway is not required for lysosomal enzyme trafficking (FIGS. 3E-3G).

Figure 4A:
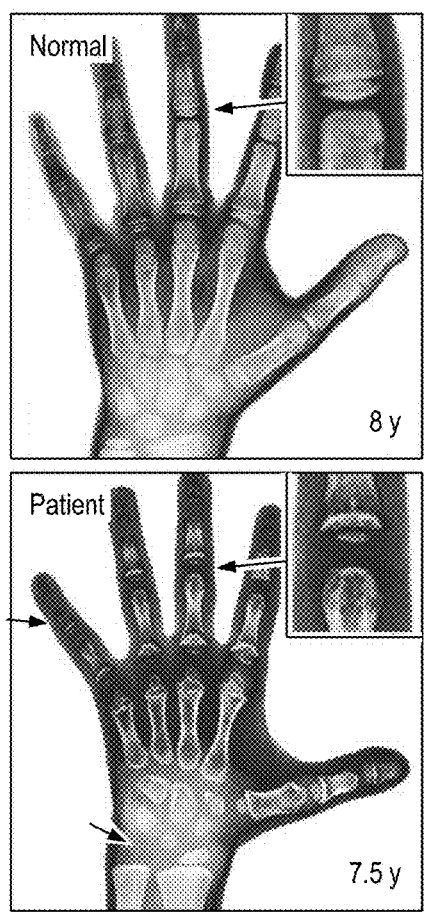
FIGS. 4A to 4I shows that S1P deficiency causes defective UPR and subsequent cell death, owing to collagen accumulation in the ER of patient chondrocytes.
Figure 4B:
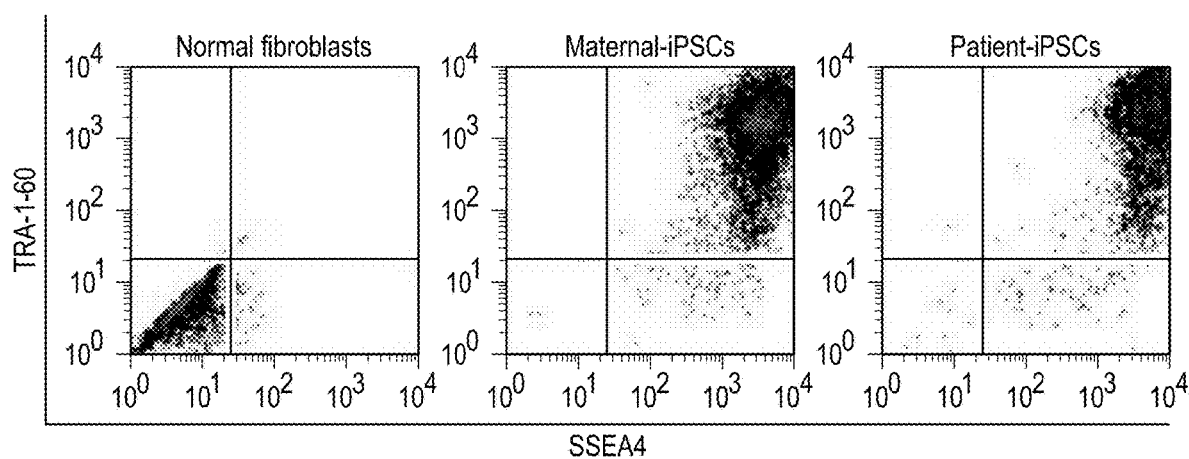
Figure 4C:
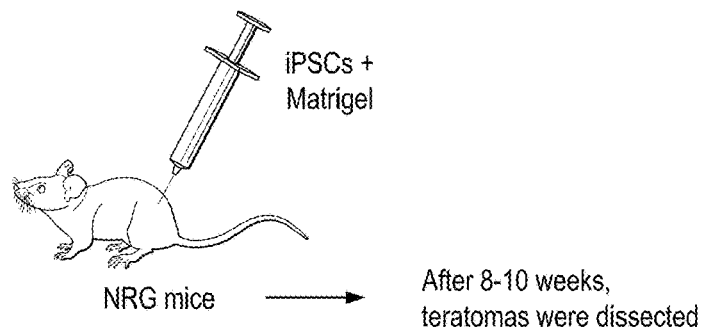
Figure 4D:
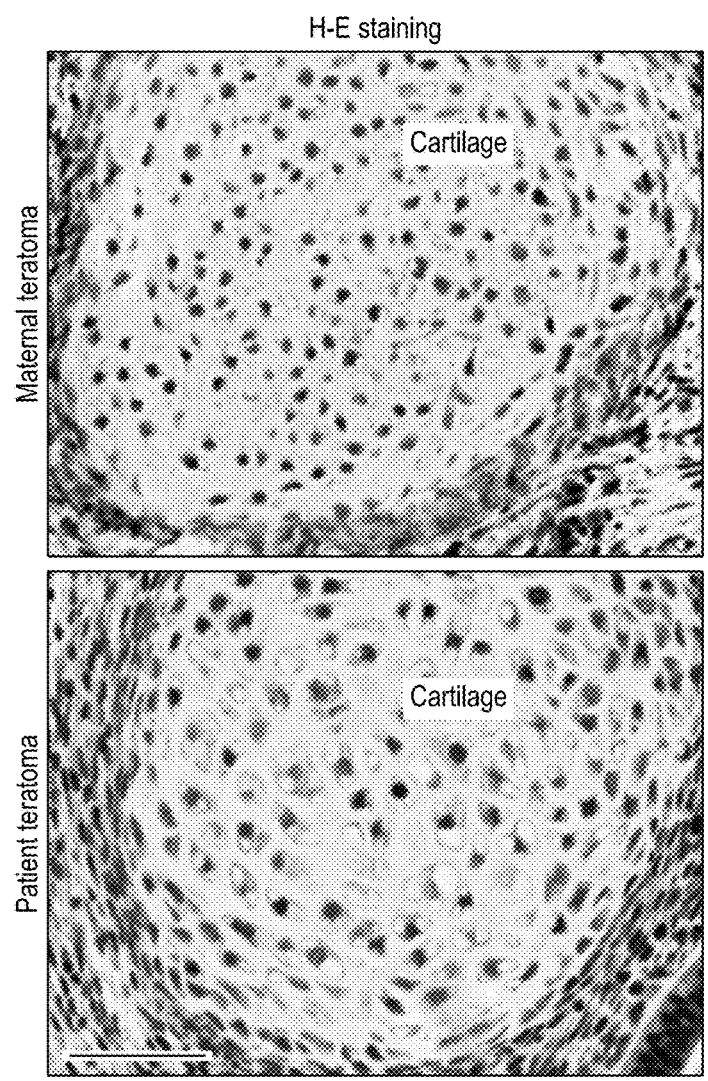
Figure 4E:
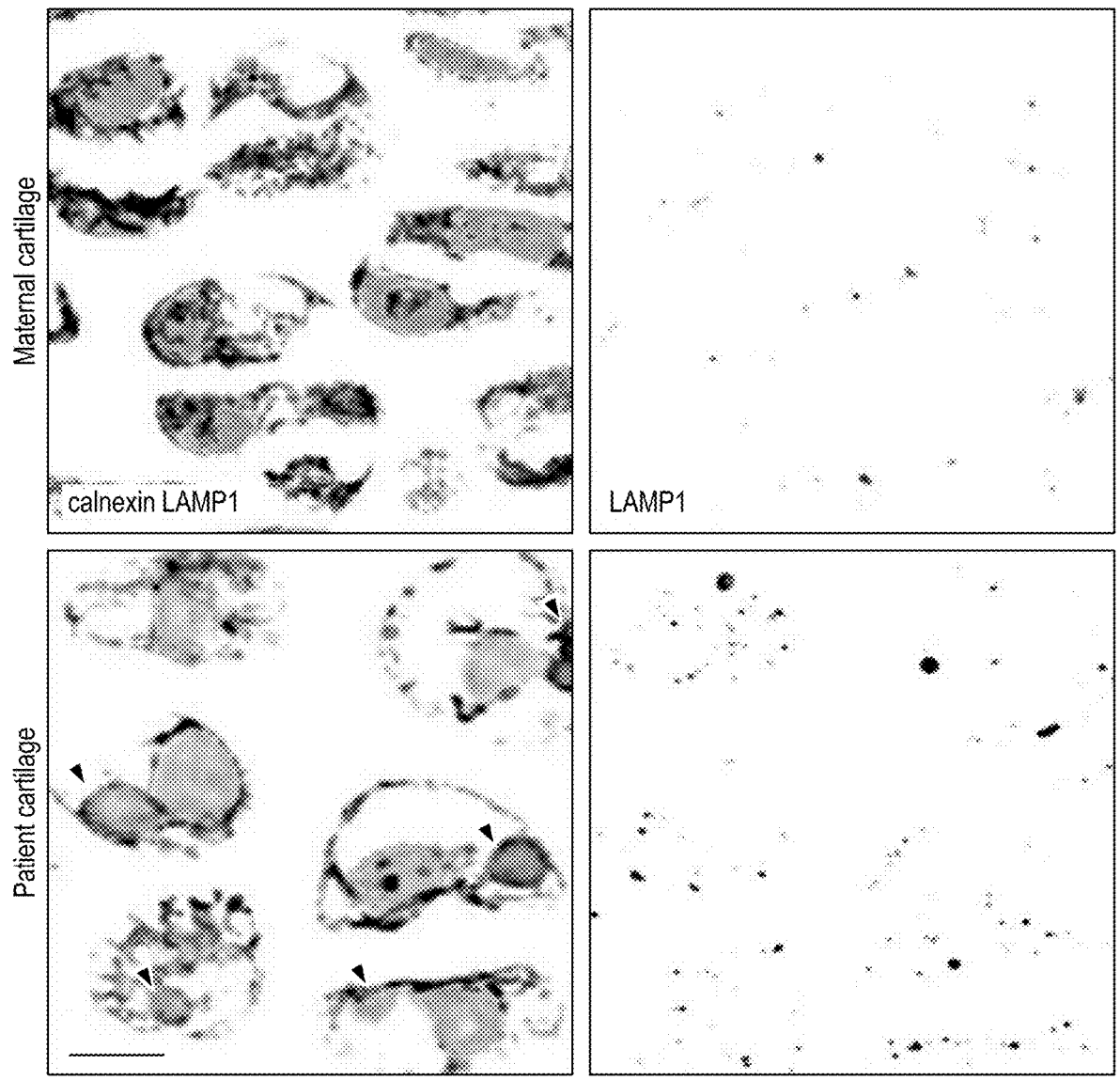
Figure 4F:
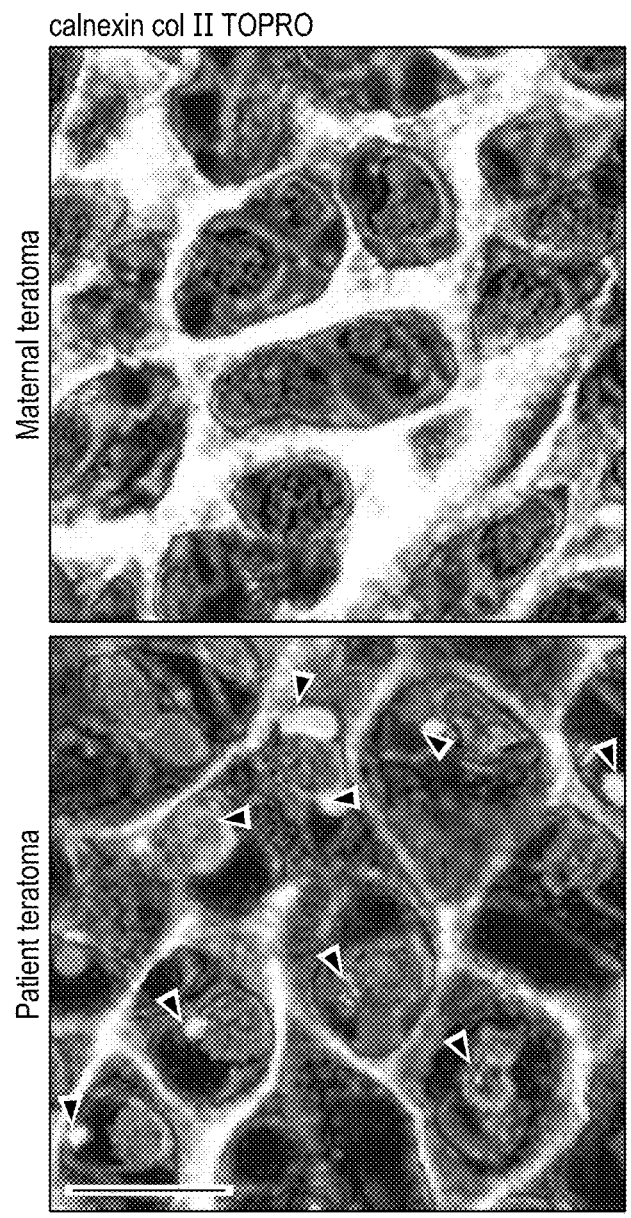
Figure 4G:
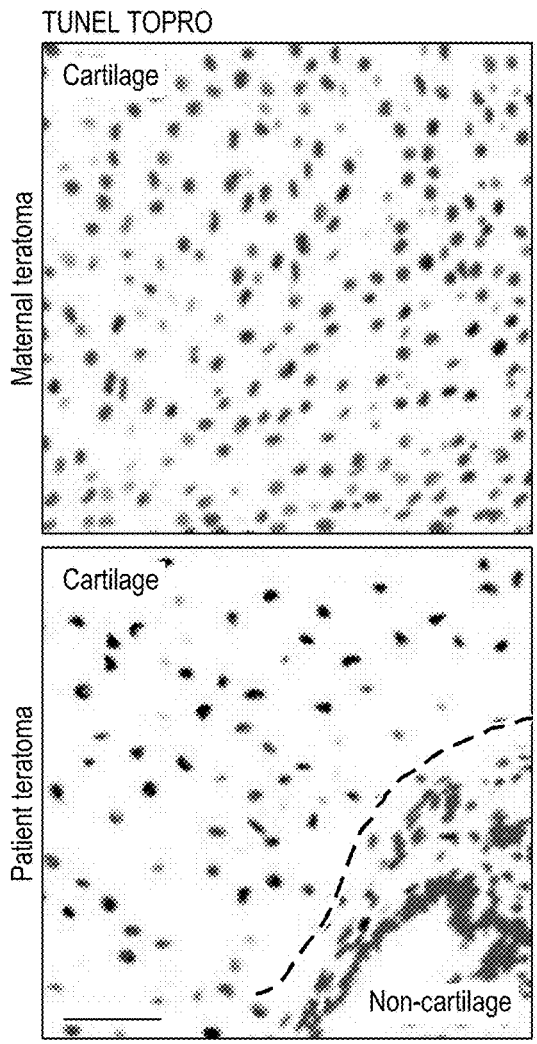
Figure 5A:
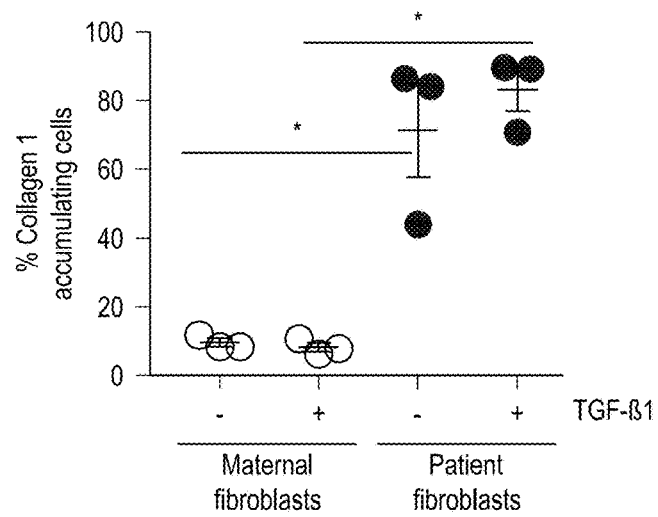
FIG. 5A to 5H shows that impaired S1P-BBF2H7-Tango1 axis causes abnormal collagen retention in the ER.
Figure 5B:
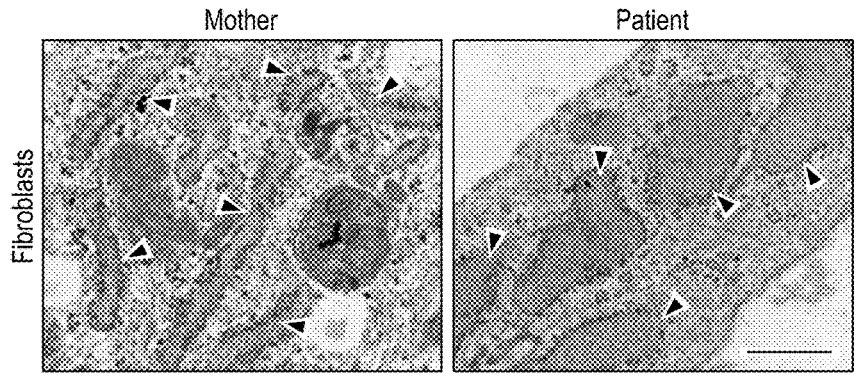

S1P deficiency causes defective UPR and subsequent cell death, owing to collagen accumulation in the ER of the patient chondrocytes. Skeletal dysplasia was the major clinical presentation of the S1P patient (FIG. 4A), and it was also observed in Mbtps1-deficient mice. S1P regulates ER stress responses (1, 3). The inventors determined that skeletal dysplasia was due to an impaired unfolded protein response (UPR), which is typically triggered by physiological ER stress during normal skeletal development to increase protein folding and secretory capacities, especially in secretory cells such as osteoblasts and chondrocytes (17, 18). To test this, the inventors generated iPSCs from primary fibroblasts from the patient and her mother (FIG. 4B). The patient iPSCs displayed defective osteoblast differentiation when compared with the maternal iPSCs and had impaired induced expression of UPR-related genes, such as HSPA5 and DDIT3 (19). The inventors used these patient- and maternal-derived iPSCs to generate teratomas (FIGS. 4C and 4D), which contain multiple tissues, including cartilages. Chondrocytes in patient iPSC-derived teratomas displayed increased lysosomes, enlarged ER, an abnormal ER retention of collagens, and increased apoptosis compared with those in maternal iPSC-derived teratomas (FIGS. 4E-4G). These phenotypes were recapitulated in patient fibroblasts treated with TGF-β1, which induces ER stress (FIG. 5A) (20). In addition, the size of the ER in patient fibroblasts was considerably enlarged compared with that of maternal fibroblasts (FIG. 5B). These data supported the hypothesis that S1P deficiency causes defective UPR and subsequent cell death, owing to collagen accumulation in the ER.

Figure 4H:
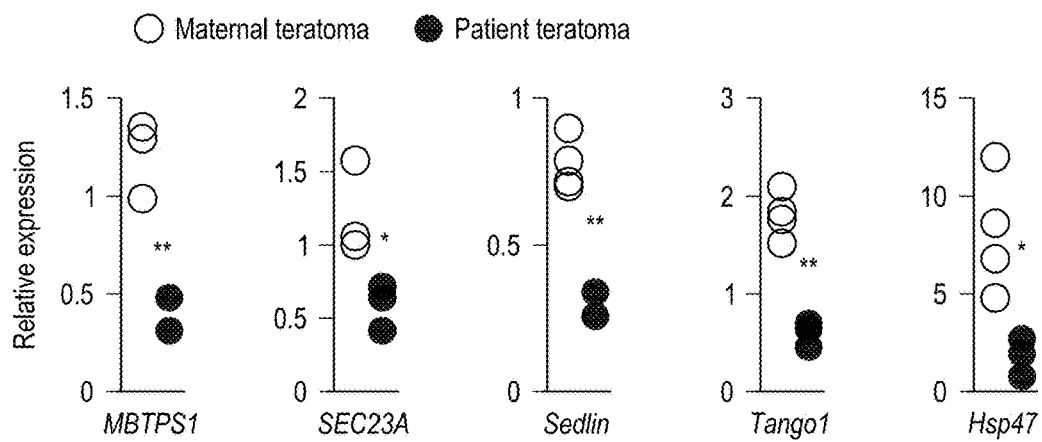
Figure 4I:
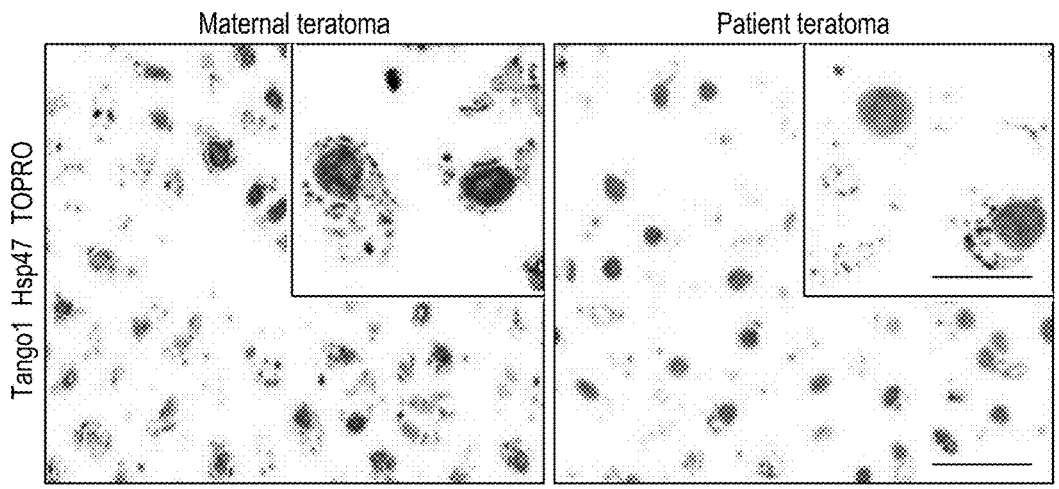
Figure 5C:
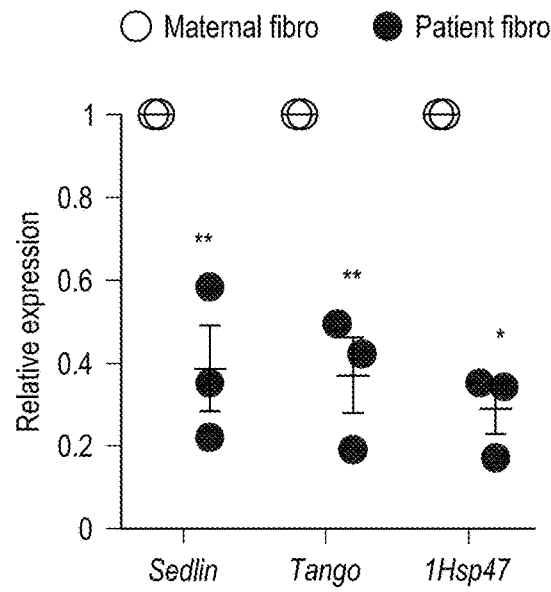
Figure 5D:
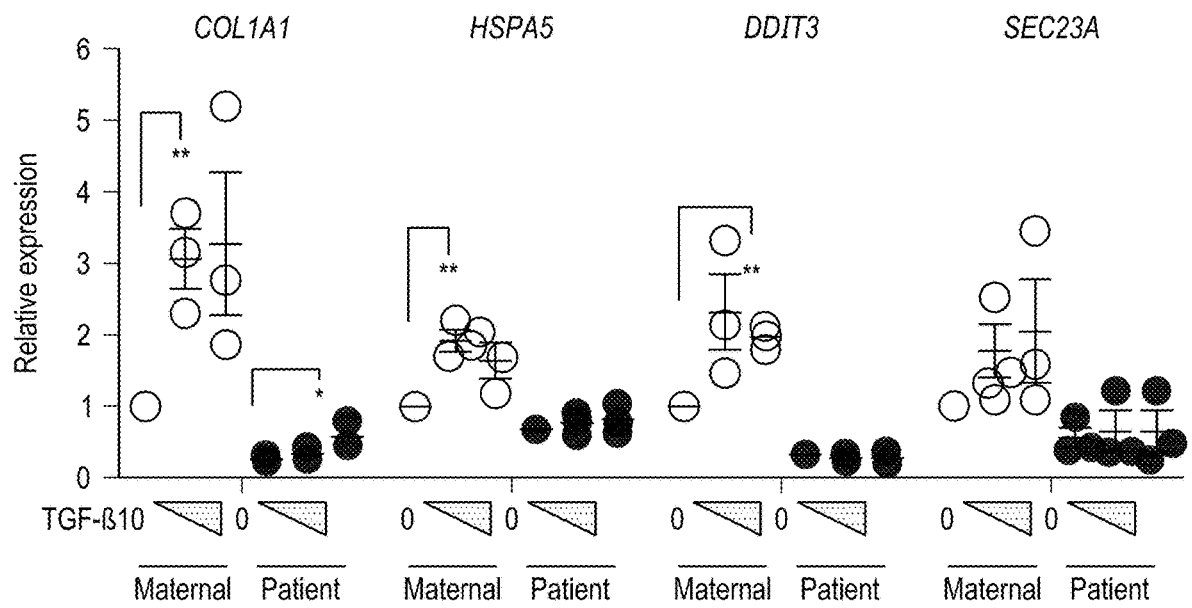
Figure 5E:
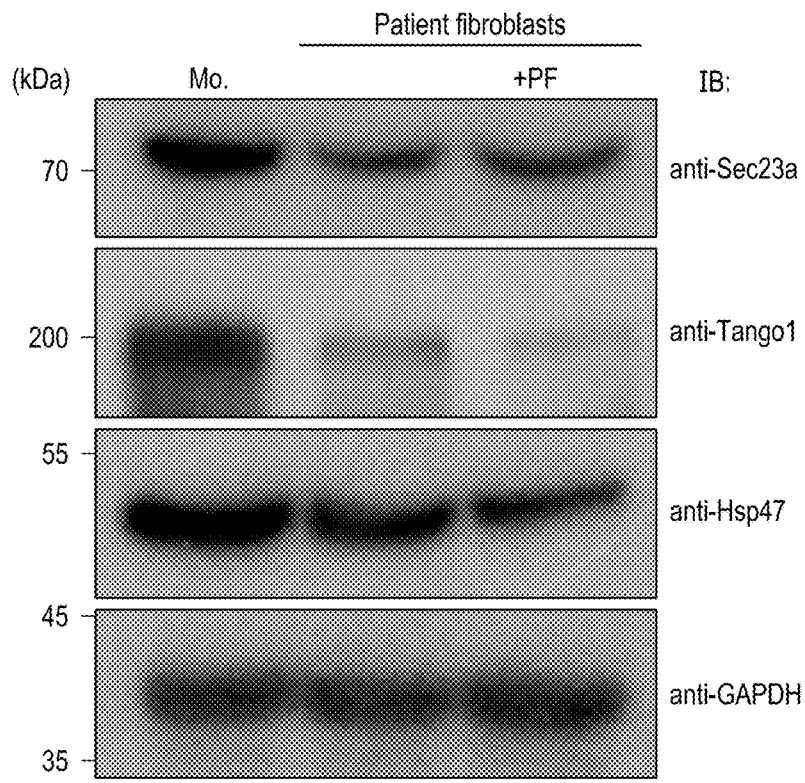
Figure 5F:
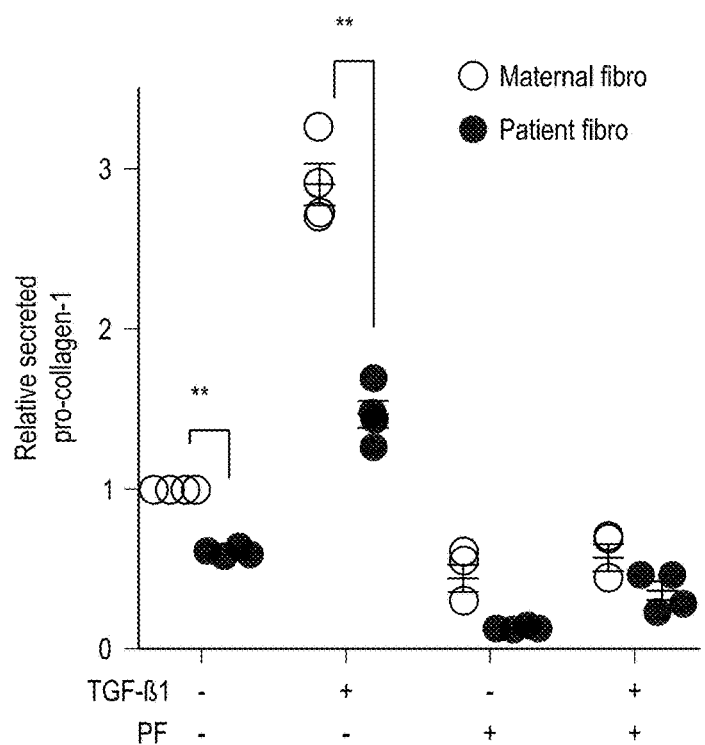
Figure 5G:
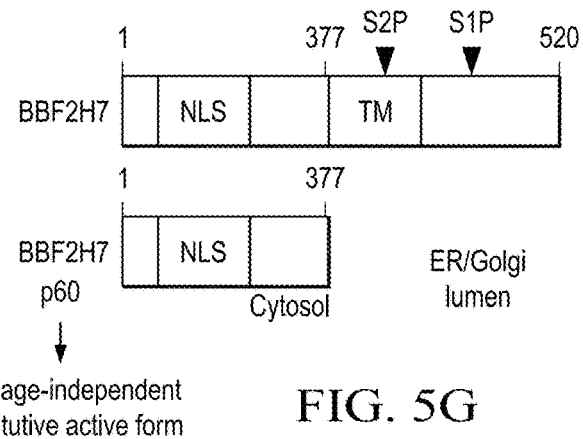
Figure 5H:
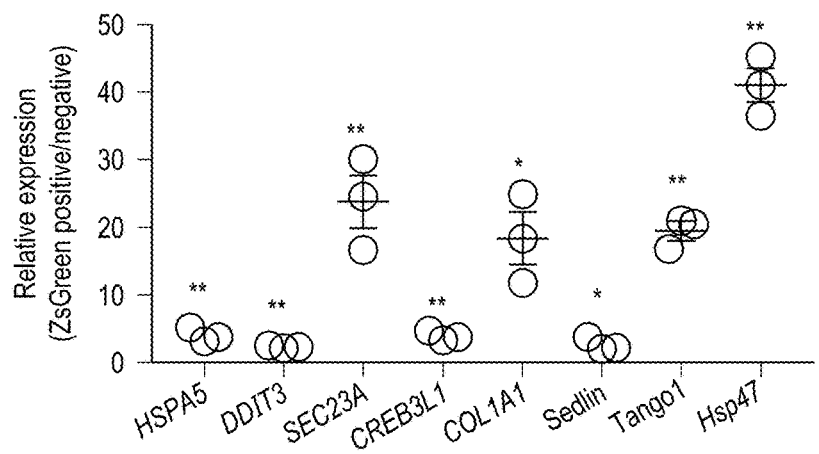

Impaired S1P-BBF2H7-Tango1 axis causes impaired mega COP-II vesicle formation essential for collagen trafficking between the ER and Golgi. Extracellular matrix (ECM) proteins are essential for skeletal development. ECM proteins are biosynthesized in the ER and transported by coat protein complex II (COP-II) vesicles to the Golgi apparatus en route to the extracellular spaces. The COP-II vesicles are typically approximately 80 nanometers in diameter. However, collagens, which are major ECM proteins for skeletal development, are over several hundred nanometers long. Therefore, specially enlarged COP-II vesicles (mega vesicles), which are regulated by the UPR, are required to export collagens to the Golgi apparatus for secretion (10, 21). S1P proteolyfically activates membrane-bound transcription factor BBF2H7, a key UPR transducer, to regulate expression of a set of genes (Sec23a, Tango1, Sedlin, and Hsp47) essential for the formation of mega vesicles in ECM-secreting cells (8, 18, 21-25). These genes were downregulated in patient teratomas and patient fibroblasts compared with controls (FIG. 4H and FIGS. 5C and 5D). As the patient fibroblasts express a residual amount of MBTPS1, the inventors treated the cells with an S1P inhibitor, which further decreased Tango1 and Hsp47 in patient fibroblasts and impaired collagen I secretion (FIGS. 5E and 5F). Importantly, Tango1 and Hsp47 were also decreased in cartilage in patient teratomas (FIG. 4I), indicating a critical role of S1P in UPR-regulated mega vesicle formation. Overexpression of a constitutively active form of BBF2H7 (p60), which is only composed of cytoplasmic domain of BBF2H7 and, thus, cleavage by S1P is not required for the translocation of p60 into the nucleus, significantly increased the expression of genes essential for the formation of mega vesicles in patient fibroblasts (FIGS. 5G and 5H), indicating that active BBF2H7 positively regulates these genes. Thus, impaired S1P-BBF2H7-Tango1-ER-axis-regulated mega vesicle formation underlies collagen retention in patient cells.

Figure 6A:
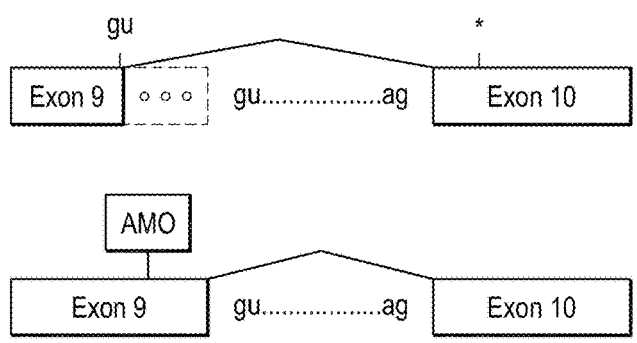
FIGS. 6A to 6F show that improving ER function or antisense morpholino oligo splicing therapy mitigates collagen retention in the ER of MBTPS1 mutant cells.

Abnormally secreted lysosomal enzyme-mediated ECM degradation contributes to skeletal dysplasia in the patient. Upon ER stress, the proteolytic activation of BBF2H7 requires sequential actions of S1P and S2P in the Golgi membrane. Patients with deficiency of S2P have been reported (26). To differentiate the S1P-deficient patient from the S2P-deficient patient, the inventors identified a new S2P-deficient patient with a short stature (26), suggesting that the skeletal dysplasia resembles the S1P-deficient patient. However, the S2P-deficient patient had no elevated levels of serum lysosomal enzymes and urine N-telopeptides, a collagen degradation product (FIG. 3F). In contrast, the S1P patient has increased levels of urine N-telopeptides, suggesting abnormal ECM degradation due to abnormally secreted lysosomal enzymes with collagenase activity in the absence of S1P. Thus, these data indicate that the defective S1P-GPT-lysosome axis plays an additional contribution to the skeletal dysplasia in this patient (FIG. 6F) (27).

Figure 6B:
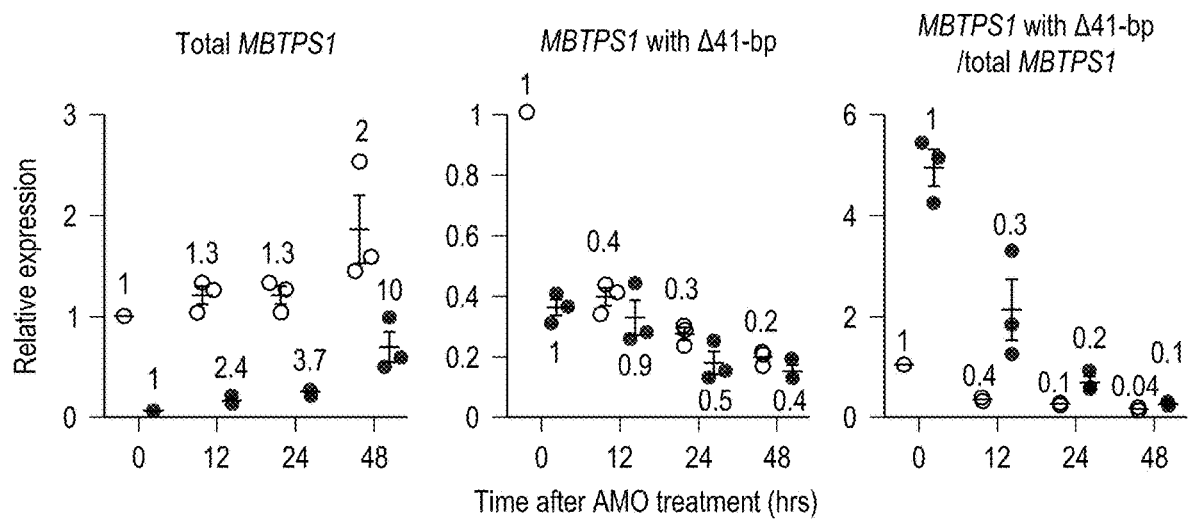
Figure 6C:
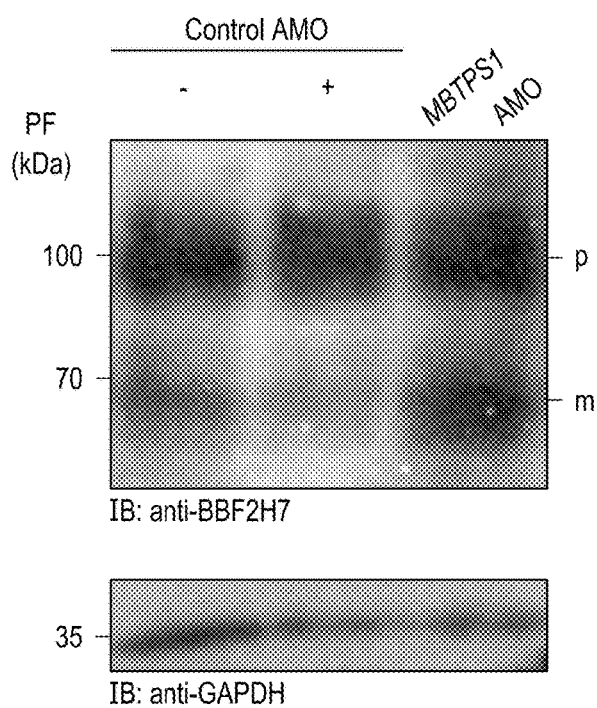
Figure 6D:
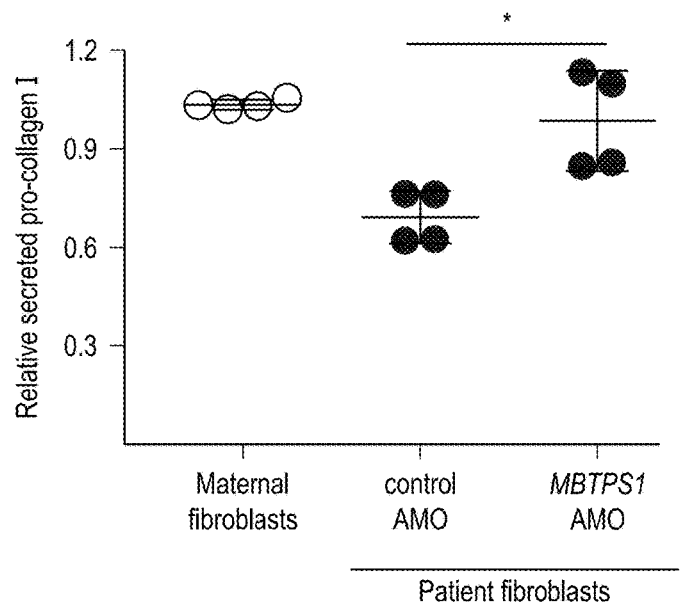

Blocking the pathogenic splicing site by AMO restored ER function in patient cells. To validate that the maternal alternative splicing site is pathogenic, the inventors treated patient fibroblasts with an antisense morpholino oligonucleotide (AMO) (FIG. 6A) (28). AMO treatment resulted in a 20-fold increase in properly spliced MBTPS1 transcripts and a substantial decrease in the 41-bp-deleted pathogenic splice variant in the patient cells compared with control oligo (FIG. 6B). AMO treatment also increased the S1P-dependent activation of BBF2H7 as well as the expression of UPR- and COP-II-related genes in patient fibroblasts (FIG. 6C). Importantly, AMO treatment increased secretion of collagen I in patient fibroblasts (FIG. 6D). These results not only validate the disease-causing variants of MBTPS1, but also reveal a potential individualized gene therapy for this patient.

Figure 6E:
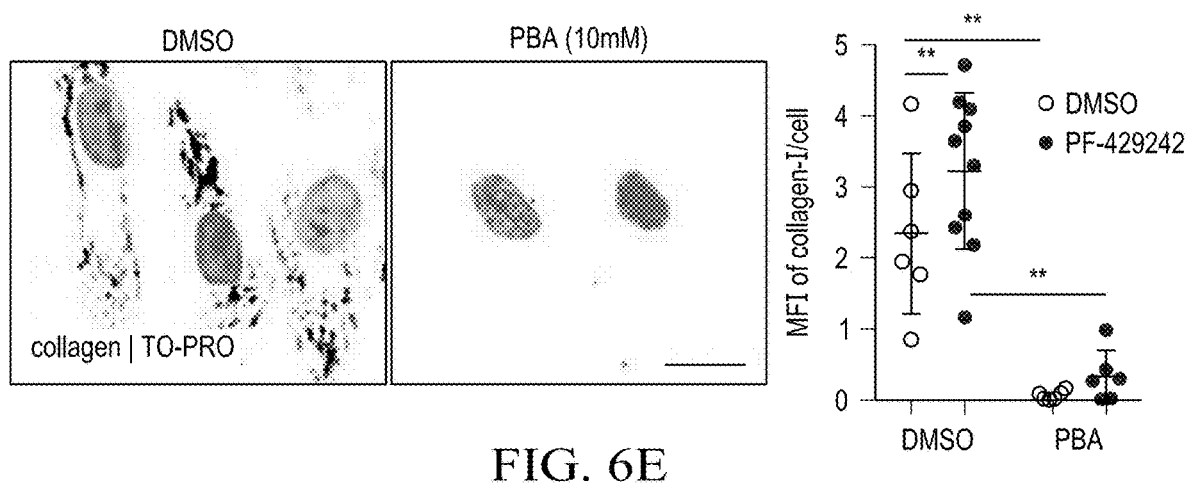
Figure 6F:
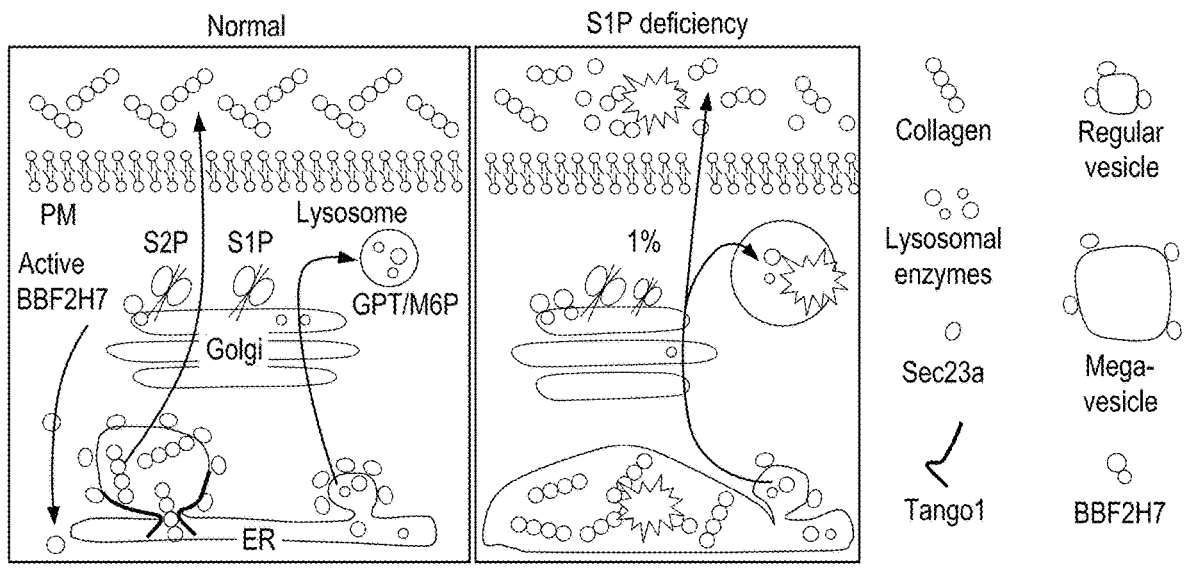

Improving ER function mitigates collagen accumulation in the ER of patient cells. To investigate whether improving ER function mitigates the S1P-deficient cellular abnormalities, the inventors tested the FDA-approved histone deacetylase inhibitor named PBA (sodium phenylbutyrate) (29). These results indicate that PBA treatment diminished collagen I accumulation in patient fibroblasts (FIG. 6E), suggesting a potential therapy to improve the skeletal developmental defects.

Figure 7A:
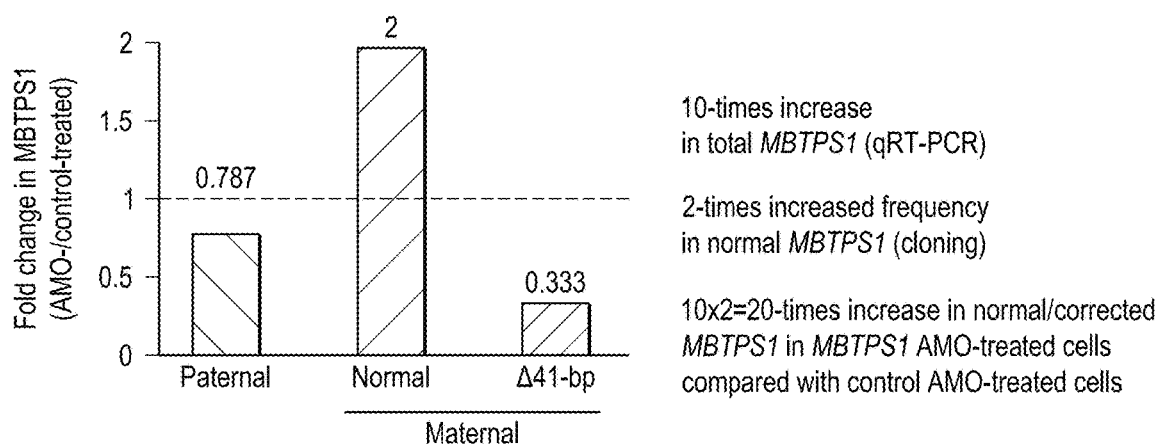
FIGS. 7A and 7B show the blocking the pathogenic splicing using AMO improves defective cellular functions of patient fibroblasts.
Figure 7B:
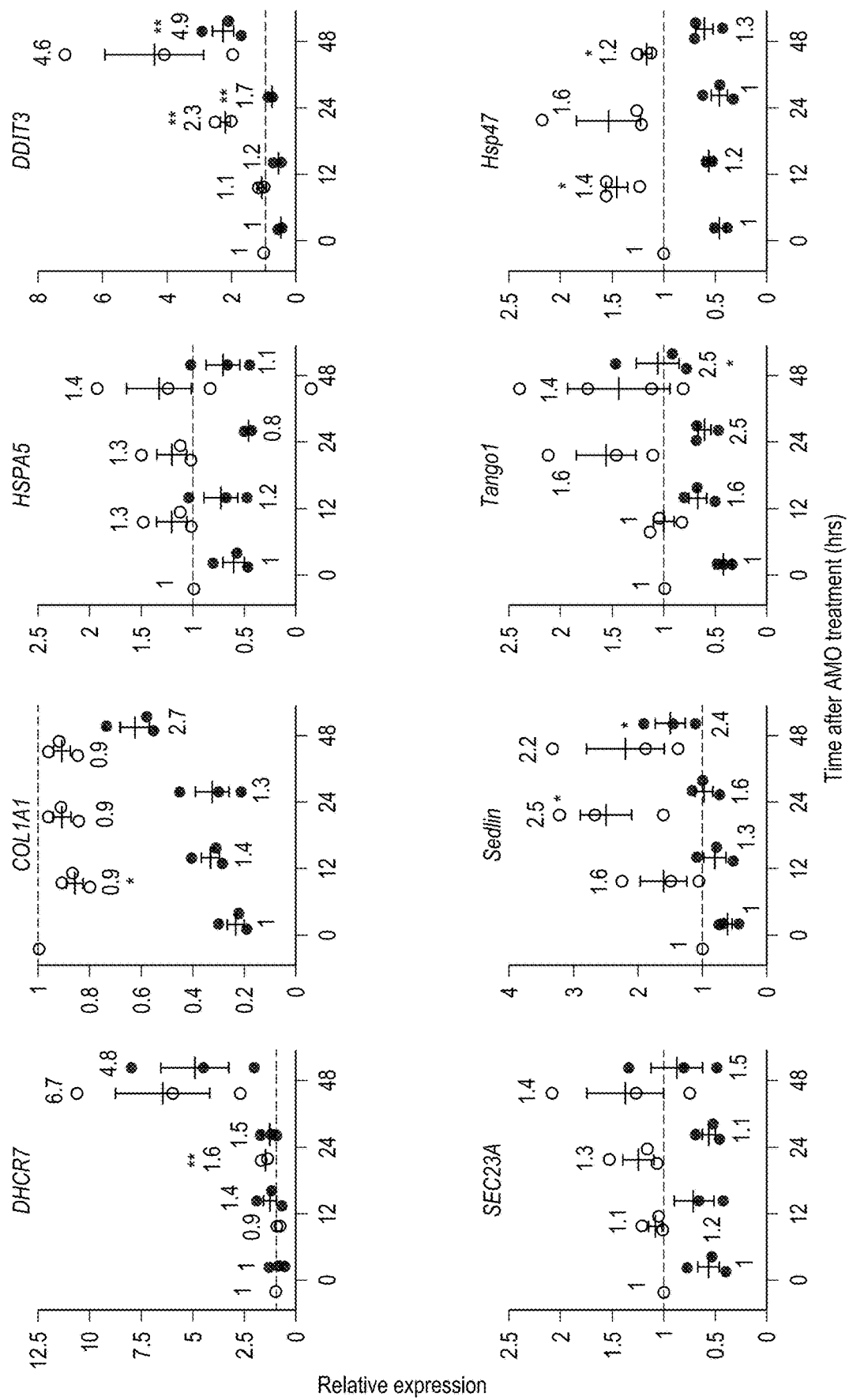

FIGS. 7A and 7B show the blocking the pathogenic splicing using AMO improves defective cellular functions of patient fibroblasts. (FIG. 7A) Summary of the DNA sequences of three forms of cloned exon 9 of MBTPS1 cDNA expressed in patient fibroblasts treated with AMO. Compared with control oligo treatment, AMO treatment increased 2-fold in correctly spliced transcript. Given that 10-fold increase of total MBTPS1 expression (data not shown), the absolute maternal transcript with a missense mutation (p.D365G) is increased 20-fold compared with control oligotreated cells. (FIG. 7B) The mRNA expression of an SREBP-regulated gene (DHCR7), collagen I (COL1A1), ER stress-related genes (HSPA5 and DDIT3), the secretory component (SEC23A) and mega vesicle components (Sedlin, Tango1 and Hsp47) were analysed by quantitative RTPCR after treatment with AMO. Blue, mother; red, the patient. The number indicates the fold change relative to time 0. Data represent means±SEM; n=3. *P<0.05, **P<0.01.

The present invention includes a pediatric patient with skeletal dysplasia and increased circulating lysosomal enzymes resulting from biallelic MBTPS1 pathogenic variants that cause S1P deficiency. Although S1P is a critical protease for activating various membrane-bound transcription factors needed to induce physiological ER stress responses that is required for normal organ development, the skeletal dysplasia present in this patient is by far the most obvious clinical manifestation. This indicates that S1P function is especially required for skeletal development.

S1P is the only enzyme to proteolytically activate GPT based on reported in vitro studies (4). It was found that S1P deficiency impaired proteolytic activation of GPT, with resultant extracellular secretion of lysosomal enzymes in cultured cells as well as in mice. However, cells with S1P deficiency had less severe lysosomal phenotypes than GPT-deficient cells. In addition, M6P modification in lysates from S1P-deficient cells was similar to those from WT cells. These data demonstrate that, although S1P plays an important role in proteolytically activating GPT (FIG. 3C), it is not the sole enzyme that has this function. Thus, future studies are necessary to identify additional new protease(s).

S1P was discovered as a critical regulator for synthesis of cholesterol and fatty acids in cultured cells and in mice (1, 3). Previous studies in mice suggest that it is a potential target for lipid-lowering drugs (7), but whether humans respond to S1P deficiency in the same way as mice has been unclear, because cholesterol metabolism is different between humans and mice. In addition, the early embryonic lethality phenotype observed in S1P-deficient mice suggests potential detrimental complications of S1P blockade. These data show that the patient did not have any obvious metabolic abnormalities and that her lipid levels were only slightly lower compared with those of controls without challenge, suggesting that the residual S1P activity is sufficient to maintain lipid homeostasis under physiological conditions.

Sec23a has been considered the target gene regulated by BBF2H7 for the formation of both regular and mega vesicles in mice (18). In contract, Tango1 and Hsp47, regulated by BBF2H7, are known to be important in mega vesicle formation (17, 30, 31). These results show that collagens but not regular cargo proteins, such as lysosomal enzymes, had defective ER-to-Golgi trafficking and secretion in the ER of the patient cells, suggesting that mega vesicle but not regular COP-II vesicle-mediated inter-organelle trafficking is impaired. These results demonstrate that reduction of BBF2H7-regulated critical targets, such as Tango1 and Hsp47, causes the impaired ER exporting of collagen, leading to defective skeletal development in the patient.

During ER stress, the proteolytic activation of S1P substrates, including BBF2H7, requires sequential actions of S1P and S2P in the Golgi membrane (1). The S2P-deficient patient identified has short stature (26), suggesting skeletal dysplasia similar to that of the S1P-deficient patient. However, the S2P-deficient patient had no elevated levels of circulating lysosomal enzymes and urine N-telopeptides, a collagen degradation product, indicating that S2P function is not required for the targeted intracellular transport of lysosomal enzymes. In contrast, the S1P patient has increased levels of urine N-telopeptides, indicating an additional contribution of abnormal ECM degradation to the skeletal dysplasia due to abnormally secreted lysosomal enzymes with bone matrix-degrading activity (32). Although most of the substrates of S1P are shared with S2P, mutations in the two genes result in widely different clinical manifestations, indicating differential function of these regulatory proteases.

These data demonstrate that a compound defect in the S1P-BBF2H7-Tango1-ER axis and S1P-GPT-lysosome axis for the pathogenesis of a new skeletal dysplasia upon loss of S1P. Importantly, this study provides insights into differential requirements of S1P functions in humans and suggests personalized therapies for this patient. Genetic skeletal diseases constitute a large and diverse group (33). Each individual disease is rare. Collectively, they are common (1 per 4,000 children) and have very few therapeutic options. ER dysfunction is common in these patients (33). These findings include a new therapy for these genetic skeletal diseases.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skill in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112 as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Brown M S, Goldstein J L. The SREBP pathway: regulation of cholesterol metabolism by proteolysis of a membrane-bound transcription factor. Cell. 1997; 89(3): 331-340.
2. Wang X, Sato R, Brown M S, Hua X, Goldstein J L. SREBP-1, a membrane-bound transcription factor released by sterol-regulated proteolysis. Cell. 1994; 77(1):53-62.
3. Ye J, et al. ER stress induces cleavage of membrane-bound ATF6 by the same proteases that process SREBPs. Mol Cell. 2000; 6(6):1355-1364.
4. Marschner K, Kollmann K, Schweizer M, Braulke T, Pohl S. A key enzyme in the biogenesis of lysosomes is a protease that regulates cholesterol metabolism. Science. 2011; 333(6038):87-90.
5. Baranski T J, Faust P L, Kornfeld S. Generation of a lysosomal enzyme targeting signal in the secretory protein pepsinogen. Cell. 1990; 63(2):281-291.
6. Steet R A, et al. A splicing mutation in the alpha/beta GlcNAc-1-phosphotransferase gene results in an adult onset form of mucolipidosis III associated with sensory neuropathy and cardiomyopathy. Am J Med Genet A. 2005; 132A(4):369-375.
7. Yang J, Goldstein J L, Hammer R E, Moon Y A, Brown M S, Horton J D. Decreased lipid synthesis in livers of mice with disrupted site-1 protease gene. Proc Natl Acad Sci USA. 2001; 98(24):13607-13612.
8. Schlombs K, Wagner T, Scheel J. Site-1 protease is required for cartilage development in zebrafish. Proc Natl Acad Sci USA. 2003; 100(24):14024-14029.
9. Achilleos A, et al. MBTPS1/SKI-1/S1P proprotein convertase is required for ECM signaling and axial elongation during somitogenesis and vertebral development†. Hum Mol Genet. 2015; 24(10):2884-2898.
10. Patra D, et al. Site-1 protease is essential for endochondral bone formation in mice. J Cell Biol. 2007; 179(4): 687-700.
11. Kudo M, Brem M S, Canfield W M. Mucolipidosis II (I-cell disease) and mucolipidosis IIIA (classical pseudo-hurler polydystrophy) are caused by mutations in the GlcNAc-phosphotransferase alpha/beta-subunits precursor gene. Am J Hum Genet. 2006; 78(3):451-463.
12. Tiede S, et al. Mucolipidosis II is caused by mutations in GNPTA encoding the alpha/beta GlcNAc-1-phosphotransferase. Nat Med. 2005; 11(10):1109-1112.

13. Tiede S, Muschol N, Reutter G, Cantz M, Ullrich K, Braulke T. Missense mutations in N-acetylglucosamine-1-phosphotransferase alpha/beta subunit gene in a patient with mucolipidosis III and a mild clinical phenotype. Am J Med Genet A. 2005; 137A(3):235-240.
14. Rodriguez-Pascau L, Coll M J, Vilageliu L, Grinberg D. Antisense oligonucleotide treatment for a pseudoexon-generating mutation in the NPC1 gene causing Niemann-Pick type C disease. Hum Mutat. 2009; 30(11): E993E1001.
15. Ran F A, Hsu P D, Wright J, Agarwala V, Scott D A, Zhang F. Genome engineering using the CRISPR-Cas9 system. Nat Protoc. 2013; 8(11):2281-2308.
16. Kollmann K, et al. Lysosomal dysfunction causes neurodegeneration in mucolipidosis II 'knock-in' mice. Brain. 2012; 135(Pt 9):2661-2675.
17. Ishikawa T, et al. UPR transducer BBF2H7 allows export of type II collagen in a cargoand developmental stage-specific manner J Cell Biol. 2017; 216(6):1761-1774.
18. Saito A, et al. Regulation of endoplasmic reticulum stress response by a BBF2H7-mediated Sec23a pathway is essential for chondrogenesis. Nat Cell Biol. 2009; 11(10):1197-1204.
19. Yamamoto K, et al. Direct conversion of human fibroblasts into functional osteoblasts by defined factors. Proc Natl Acad Sci USA. 2015; 112(19):6152-6157.
20. Kim S I, Na H J, Ding Y, Wang Z, Lee S J, Choi M E. Autophagy promotes intracellular degradation of type I collagen induced by transforming growth factor (TGF)-β1. J Biol Chem. 2012; 287(15):11677-11688.
21. Ishikawa Y, Ito S, Nagata K, Sakai L Y, Bächinger H P. Intracellular mechanisms of molecular recognition and sorting for transport of large extracellular matrix molecules. Proc Natl Acad Sci USA. 2016; 113(41):E6036-E6044.
22. Venditti R, et al. Sedlin controls the ER export of procollagen by regulating the Sar1 cycle. Science. 2012; 337(6102):1668-1672.
23. Kondo S, et al. BBF2H7, a novel transmembrane bZIP transcription factor, is a new type of endoplasmic reticulum stress transducer. Mol Cell Biol. 2007; 27(5):1716-1729.
24. Masago Y, et al. The molecular chaperone Hsp47 is essential for cartilage and endochondral bone formation. J Cell Sci. 2012; 125(Pt 5):1118-1128.
25. Wilson D G, et al. Global defects in collagen secretion in a Mia3/TANGO1 knockout mouse. J Cell Biol. 2011; 193(5):935-951.
26. Lindert U, et al. MBTPS2 mutations cause defective regulated intramembrane proteolysis in X-linked osteogenesis imperfecta. Nat Commun. 2016; 7:11920.
27. Petrey A C, et al. Excessive activity of cathepsin K is associated with cartilage defects in a zebrafish model of mucolipidosis II. Dis Model Mech. 2012; 5(2):177-190.
28. Osorio F G, et al. Splicing-directed therapy in a new mouse model of human accelerated aging. Sci Transl Med. 2011; 3(106):106ra107.
29. Rishikof D C, Ricupero D A, Liu H, Goldstein R H. Phenylbutyrate decreases type I collagen production in human lung fibroblasts. J Cell Biochem. 2004; 91(4):740-748.
30. Maeda M, Saito K, Katada T. Distinct isoform-specific complexes of TANGO1 cooperatively facilitate collagen secretion from the endoplasmic reticulum. Mol Biol Cell. 2016; 27(17):2688-2696.
31. Saito K, et al. TANGO1 facilitates cargo loading at endoplasmic reticulum exit sites. Cell. 2009; 136(5):891-902.
32. Kollmann K, et al. Decreased bone formation and increased osteoclastogenesis cause bone loss in mucolipidosis II. EMBO Mol Med. 2013; 5(12):1871-1886.
33. Briggs M D, Bell P A, Wright M J, Pirog K A. New therapeutic targets in rare genetic skeletal diseases. Expert Opin Orphan Drugs. 2015; 3(10):1137-1154.
34. Bergstrom K, et al. Defective intestinal mucin-type O-glycosylation causes spontaneous colitis-associated cancer in mice. Gastroenterology. 2016; 151(1):152-164.e11.
35. Rawson R B, DeBose-Boyd R, Goldstein J L, Brown M S. Failure to cleave sterol regulatory element-binding proteins (SREBPs) causes cholesterol auxotrophy in Chinese hamster ovary cells with genetic absence of SREBP cleavage-activating protein. J Biol Chem. 1999; 274(40): 28549-28556.
36. Okita K, et al. A more efficient method to generate integration-free human iPS cells. Nat Methods. 2011; 8(5):409-412.
37. Herzog B H, et al. Podoplanin maintains high endothelial venule integrity by interacting with platelet CLEC-2. Nature. 2013; 502(7469):105-109.
38. Du L, Pollard J M, Gatti R A. Correction of prototypic ATM splicing mutations and aberrant ATM function with antisense morpholino oligonucleotides. Proc Natl Acad Sci USA. 2007; 104(14):6007-6012.
39. Delitto D, et al. Human pancreatic cancer cells induce a MyD88-dependent stromal response to promote a tumor-tolerant immune microenvironment. Cancer Res. 2017; 77(3):672-683.

The invention claimed is:

1. A method of treating a bone disease in a human caused by an intracellular protein trafficking defect comprising:
   identifying a human subject having the bone disease caused by the intracellular protein trafficking defect in a membrane bound transcription factor peptidase, site 1 (MBTPS1) gene comprising elevated levels of blood lysosomal enzymes and skeletal dysplasia; and
   providing the human subject with an effective amount of a composition that bypasses or corrects a defect in MBTPS1 gene expression, gene splicing, or corrects lysosomal protein trafficking wherein the composition comprises a chemical chaperone selected from the group consisting of phenylbutyrate, glycerol phenyl butyrate, sodium phenyl butyrate, and tauroursodexoycholate (TUDCA).

2. The method of claim 1, wherein the composition comprises an expression vector that expresses at least one of: a MBTPS1 gene, a BBF2 human homolog on chromosome 7 (BBF2H7) transcription factor, Sec23a, Tangos, Sedlin, or Hsp47.

3. The method of claim 1, wherein the amount of the composition induces immunoglobulin heavy-chain binding protein (BiP) expression that improves osteogenicity from mesenchymal stem cells (MSCs) differentiated from iPSCs obtained from the subject.

* * * * *